US006338559B1

(12) United States Patent
Williams et al.

(10) Patent No.: US 6,338,559 B1
(45) Date of Patent: Jan. 15, 2002

(54) APPARATUS AND METHOD FOR IMPROVING VISION AND RETINAL IMAGING

(75) Inventors: David R. Williams, Fairport; Geun-Young Yoon; Antonio Guirao, both of Rochester, all of NY (US)

(73) Assignee: University of Rochester, Rochester, NY (US)

(*) Notice: Subject to any disclaimer, the term of this patent is extended or adjusted under 35 U.S.C. 154(b) by 0 days.

(21) Appl. No.: 09/559,643

(22) Filed: Apr. 28, 2000

(51) Int. Cl.[7] .............................................. A61B 3/10
(52) U.S. Cl. .................................................... 351/212
(58) Field of Search ................................ 351/205, 206, 351/212, 219, 221, 246, 160 R, 176, 177; 604/4, 5; 359/645, 716

(56) References Cited

U.S. PATENT DOCUMENTS

| | | | | |
|---|---|---|---|---|
| 5,777,719 A | * | 7/1998 | Williams et al. ............ | 351/212 |
| 5,835,279 A | * | 11/1998 | Marshall et al. ............ | 359/645 |
| 6,086,204 A | * | 7/2000 | Magnante .................... | 351/212 |
| 6,089,711 A | * | 7/2000 | Blankenbecler et al. | 351/160 R |

* cited by examiner

Primary Examiner—George Manuel
(74) Attorney, Agent, or Firm—Blank Rome Comisky & McCauley LLP

(57) ABSTRACT

A method for improving the visual performance of a person involves correcting higher-order monochromatic aberrations in combination with the correction of chromatic aberration. Such correction results in a visual benefit greater than that realized by correcting only the higher-order monochromatic aberrations or the chromatic aberration alone. The higher-order monochromatic aberrations are corrected by introducing appropriate phase profiles to compensate for the wavefront aberrations of the eye. This compensation can be provided by contact lenses, IOLs, inlays and onlays having appropriate surface shapes or by corneal shaping achieved through refractive surgery or other techniques. Chromatic aberration can be corrected by spectral filtering or artificial apodization. An apodization filter is described that provides a non-uniform amplitude transmission across the pupil of the eye. Contact lenses or other ocular devices for correcting higher-order monochromatic aberrations may include an appropriate apodization filter for correcting chromatic aberration, or an external optical device for correcting chromatic aberration may be used in combination with a contact lens, etc. for correcting the higher-order monochromatic aberrations. A device and method for improved retinal imaging is also described.

68 Claims, 14 Drawing Sheets

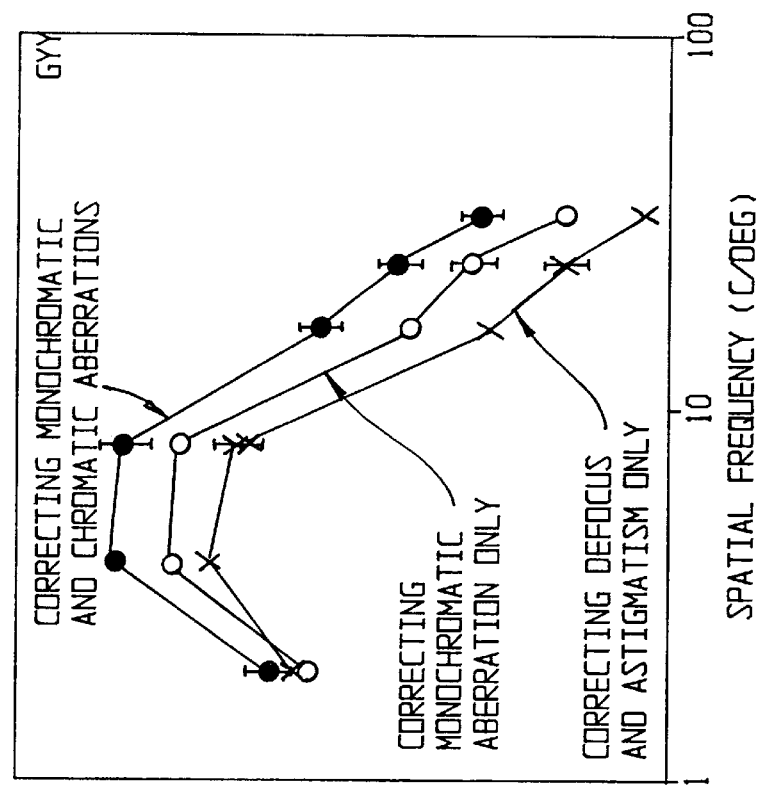
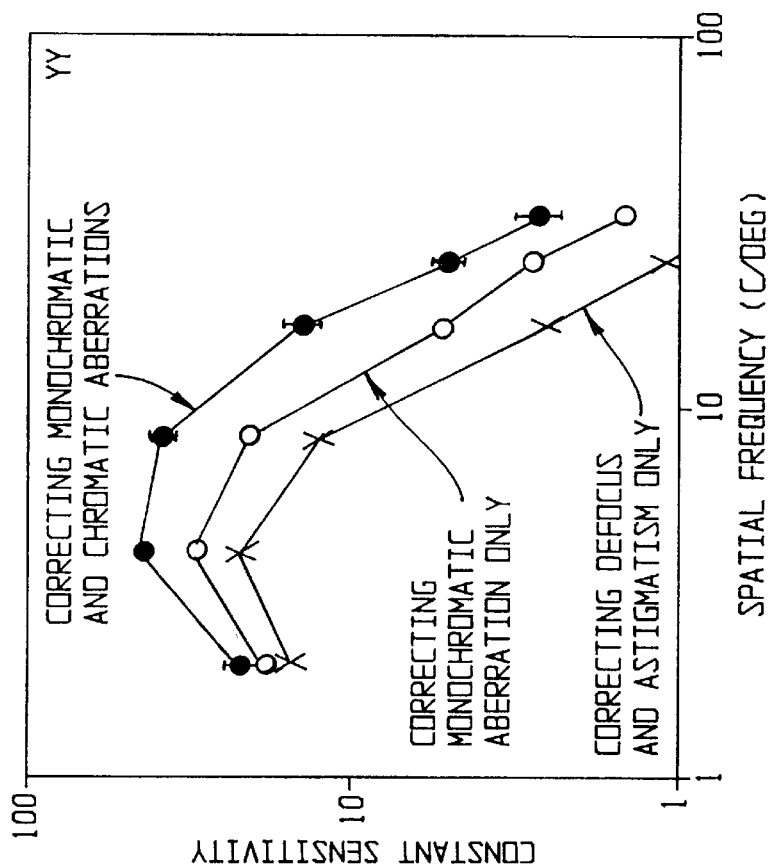
FIG. 17A
FIG. 17B

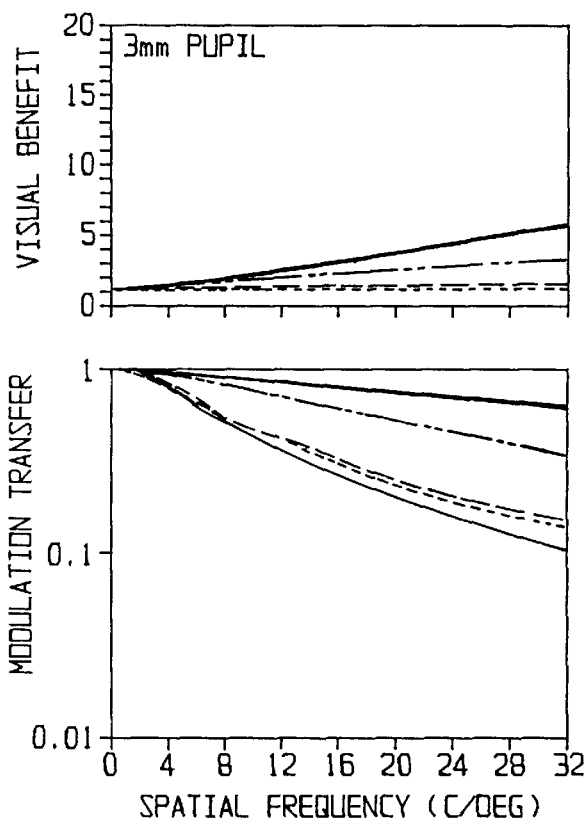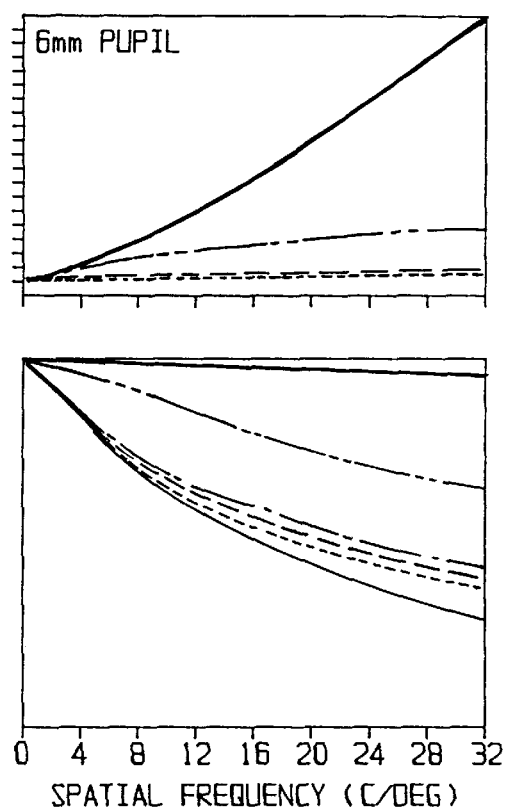
FIG. 22B  FIG. 22D
FIG. 22A  FIG. 22C
——————— CORRECTING ALL ABERRATIONS
—·—·—·— CURRENT MONOCHROMATIC ABERRATION ONLY
————— CORRECTING LCA AND TCA ONLY
— — — — CORRECTING LCA ONLY
---------- CORRECTING TCA ONLY
▬▬▬▬▬ CORRECTING DEFOCUS AND ASTIGMATISM ONLY

APPARATUS AND METHOD FOR IMPROVING VISION AND RETINAL IMAGING

This invention was made with government support through the following grants: EY04367 and EY01319 awarded by the National Eye Institute, and NSF AST 9876783 awarded by the National Science Foundation. The government has certain rights in the invention.

BACKGROUND OF THE INVENTION

1. Field of the Invention

The present invention is directed to devices and methods for improving vision and retinal imaging, and particularly, to such devices and methods for improving a person's vision and retinal imaging by correcting higher-order monochromatic ocular aberrations and ocular chromatic aberrations.

2. Description of Related Art

Despite significant advances in spectacle and contact lens design, ophthalmic lenses for the most part only correct up to the second-order ocular aberrations known as defocus and astigmatism. Higher-order monochromatic ocular aberrations such as spherical aberration, coma, and a variety of irregular aberrations are left uncorrected by spectacles, contact lenses, corneal reshaping, inlays, onlays and other current vision correction techniques. These higher order aberrations of the eye blur images formed on the retina resulting in degraded visual performance, and also blur images taken of the living human retina. Until recently there did not exist a rapid or efficient device or approach for quantitatively measuring the irregular higher-order aberrations of the eye, nor have there been made available any practical mechanisms to correct the monochromatic aberrations of the eye other than defocus and astigmatism.

Liang et al., J. Opt. Soc. Am. A., Volume 11, Number 7, pp. 1949–1957, July 1994, the disclosure of which is incorporated by reference herein, disclosed a Hartmann-Shack wavefront sensor that they used to measure the monochromatic wave aberrations of the human eye. They did this by sensing the wavefront emerging from the eye produced by the retinal reflection of a focused light beam on the fovea. Using the system disclosed therein, the authors were able to measure only up to fourth-order polynomial functions. However, the wavefront fitting with polynomials only up to fourth order does not provide a complete description of the eye's aberrations. Subsequently, Williams, et al. U.S. Pat. No. 5,777,719, the disclosure of which is incorporated by reference herein in its entirety, described an improvement on the wavefront sensor used by Liang et al. that provided measurement data and correction for at least fifth-order monochromatic aberrations and higher. By using a deformable mirror in combination with their modified wavefront sensor apparatus, Williams et al. were able to measure and correct for complex aberrations that are not conventionally corrected by spectacles, contact lenses, other ocular devices, or surgical modification of the eye. In addition, as described therein, Williams et al. described a system that provided retinal images of an unprecedented quality.

Liang et al. Supernormal vision and high resolution retinal imaging through adaptive optics. J. Opt. Soc. Am. A., 14, 2884–2892 (1997) describe the use of adaptive optics to measure and correct the monochromatic wave aberrations of the eye. They found that correcting the higher order monochromatic aberrations provided a six-fold increase in contrast sensitivity when viewing a monochromatic grating with 27.5 cycles per degree (cpd) through a 6.0 mm pupil. However, they measured contrast sensitivity only in monochromatic light and at one spatial frequency, which are not representative of normal everyday viewing conditions.

It is also well known that the human eye suffers from chromatic aberrations. There are numerous references about attempts to analyze the effect of chromatic aberration on vision. Campbell and Gubish, J. Physiol., 192, pp. 345–358 (1967) reported, with respect to chromatic difference of focus (longitudinal chromatic aberration), that there was insignificant improvement in contrast sensitivity between white light and monochromatic light over a 10 to 40 cpd range of spatial frequencies.

Thibos et al., Optometry and Vision Science, 68, 8, pp. 599–607 (1991) asked the question whether chromatic aberration significantly affects vision, and if so, how, why and by how much? They concluded that a) axial (longitudinal) chromatic aberration results in only moderate contrast sensitivity reduction and minor visual acuity loss; b) chromatic difference of magnification has little effect on visual performance; and c) transverse chromatic aberration is significant for foveal vision only when the pupil is laterally displaced. The prevailing explanation for the unremarkable impact of chromatic aberration on vision was that chromatic aberration is most severe at the spectral extremes where the photopic spectral sensitivity of the eye is low.

Furthermore, the many studies that have looked into the effect of chromatic aberration on vision and retinal image quality have not considered the synergistic effect of chromatic aberration and higher-order monochromatic aberrations on visual performance.

In an effort to improve vision, the inventors have recognized a need to evaluate visual performance under normal viewing conditions and, consequently, to determine the extent to which the correction of only second-order aberrations, higher-order aberrations, or chromatic aberration, either alone or in combination, effect an improvement in visual ability. Accordingly, there is a need for methods and apparatus to evaluate the affects of aberrations on human vision, and which provide better vision and retinal imaging through aberration correction.

SUMMARY OF THE INVENTION

The present invention is generally directed to device and method embodiments for improving human visual performance and retinal imaging, and more particularly, such devices and methods are directed to the evaluation and improvement of human visual performance and higher quality retinal imaging based upon the combined correction of higher-order monochromatic aberrations and chromatic aberration.

An embodiment of the invention is described by an optical system for improving a person's vision that includes a higher-order phase compensation element and a light amplitude modifying element. A higher-order phase compensation element can be used to provide higher order monochromatic aberration correction, while a light amplitude modifying element can be used to provide correction for chromatic aberration. In an aspect of this embodiment the higher-order phase compensation element and the light amplitude modifying element are resident in a common optical component. In an alternative aspect, the higher-order phase compensation element and the light amplitude modifying element are each resident in a separate optical component.

Another embodiment of the invention is directed to an ocular component for improving a person's visual ability.

The component has at least a shape adapted to correct a measured higher-order monochromatic ocular aberration. In addition, the ocular component has a non-uniform transmission over at least a portion of a surface thereof for correcting an ocular chromatic aberration. In an aspect of this embodiment, the pupil diameter of the eye is effectively reduced by artificial apodization to attenuate the detrimental effects of aberrations on the eye's visual performance.

Another embodiment of the invention is directed to providing improved high resolution images of the retina. The system for producing such images can advantageously use a broadband light source for increased illumination, while image quality is enhanced by correcting higher-order monochromatic aberrations and chromatic aberration.

A method embodiment of the invention is directed to improving a person's measurable visual benefit and includes correcting ocular higher-order monochromatic aberrations and in addition correcting chromatic aberration, preferably and substantially axial chromatic aberration. Preferred methods for correcting the higher-order monochromatic aberrations include providing a deformable mirror or other phase compensating element such as, e.g., an LCD or a MEMS device, or more preferably, a contact lens, an IOL, an inlay, an onlay, or corneal shaping by refractive surgery or photoablation, for example, all of which suitably are adapted to provide appropriate phase compensation to correct the aberrated wavefront generated by a typical eye. Methods for correcting chromatic aberration include spectral filtering in various forms and, preferably, artificial apodization, as will be described in greater detail below.

In order to more accurately and distinctly describe the invention, the following definitions, used throughout the description and in the appended claims, will have the meanings set forth below.

Apodization refers to a non-uniform amplitude transmission of light across the pupil radius; i.c., between the center of the pupil and the edge of the pupil.

Higher-order monochromatic aberrations refer to optical aberrations represented by third and higher-order radial Zernicke polynomials (excluding piston, tip, and tilt) or equivalent aberrations as described by another metric as understood by those skilled in the art; and where noted, refer more particularly to the optical aberrations represented by fifth to tenth-order radial Zernicke modes (excluding piston, tip, and tilt) or their equivalents.

Chromatic aberration is defined conventionally as that term is understood by a person skilled in the art, but preferably and substantially refers to axial or longitudinal chromatic aberration.

Visual performance, as referred to herein, is a qualitative reference to how well a person can see. Visual benefit (VB) will be used to denote a quantitative measure of visual performance. Visual benefit is presented in terms of contrast sensitivity and visual acuity as those terms will be understood by a person skilled in the art. More particularly, visual benefit is defined equally in terms of a psycho-physical visual benefit ($VB_{psy}$) and an optical visual benefit ($VB_{opt}$), as follows:

$$VB_{psy} \equiv \frac{CSF_{w/HOC}}{CSF_{w/oHOC}} = \frac{MTF_{w/HOC} \times \text{neural } CSF}{MTF_{w/oHOC} \times \text{neural } CSF} = VB_{opt} \equiv \frac{MTF_{w/HOC}}{MTF_{w/oHOC}}$$

where CSF is defined as contrast sensitivity function, w/HOC means with higher-order aberration correction, w/oHOC means without higher-order correction, and MTF refers to modulation transfer function. With regard to the results presented below for the case of (a) correcting only the higher-order monochromatic aberrations (third to tenth order Zernicke modes), optical visual benefit is defined as $$\text{visual benefit}_{optical} \equiv \frac{MTF_{white\ light\ w/o\ monochromatic\ aberration}}{MTF_{white\ light\ w/\ monochromatic\ aberration}};$$

and, for the case of (b) correcting both higher order monochromatic aberrations and axial chromatic aberration, optical visual benefit is defined as $$\text{visual benefit}_{optical} \equiv \frac{MTF_{monochromatic\ light\ w/o\ monochromatic\ aberration}}{MTF_{white\ light\ w/\ monochromatic\ aberration}}.$$

In both cases. defocus and astigmatism (second order Zernicke mode) were corrected as necessary to provide baseline visual performance.

An optical system refers to one or more optical elements associated with a person's vision and includes, but is not limited to, the eye or refractive parts thereof including the cornea, a contact lens, an IOL, an ocular inlay. an ocular onlay, or an external component such as. e.g., a deformable mirror or a spectacle lens, any of which may be used alone or in combination with any other optical element depending on desired applications and practical considerations.

A higher-order phase compensation element refers to, but is not limited to, any of the optical elements listed above having a surface whose shape is modified in response to higher-order monochromatic aberration wavefront data to yield a substantially plane wavefront or, in other words, to provide correction for the higher-order aberrations. A deformable mirror or other type of phase compensating device (e.g., LCD, MEMS, etc.) is included in this definition.

A light amplitude modifying element refers to, but is not limited to. a structure which redistributes light by diffraction, interference. absorption, transmission, or filtering and provides compensation for, or correction of, ocular chromatic aberration.

In summary, the invention is directed to devices and methods for obtaining a visual benefit, by correcting higher-order monochromatic aberrations and chromatic aberrations of the eye, that is greater than the visual benefit obtained by correcting either the higher-order monochromatic aberrations or chromatic aberration alone. It has been observed by the inventors that the beneficial effect provided by correcting higher-order monochromatic aberrations is diluted by the presence of chromatic aberration under normal viewing conditions. In other words, the benefit of correcting both the higher-order monochromatic ocular aberrations and ocular chromatic aberration is significantly greater than the benefit obtained by correcting either aberration alone. In addition, the dilution (or improvement) is more significant for larger pupil sizes (~3–8 mm) than for smaller pupil sizes (<3 mm). Based upon these findings, it should be possible to correct higher-order monochromatic aberrations of the eye with a DM, a contact lens, an IOL, corneal shaping. an ocular inlay, an ocular onlay, and other ocular devices or techniques known to those skilled in the art, and to further improve visual benefit by additionally correcting chromatic aberration in the eye.

The invention is also directed to a device and method for improved retinal imaging in which the above concepts are employed.

These and other objects of the invention, and the ensuing advantages. will be described more completely in the following detailed description and with respect to the related figures and the appended claims.

BRIEF DESCRIPTION OF THE DRAWINGS

FIGS. 17A, 17B are graphs of contrast sensitivity versus spatial frequency when certain aberrations are absent/present;

FIGS. 22A, 22B are graphs of MTFs and visual benefit, respectively, as a function of spatial frequency from 17 subjects' eyes at a pupil diameter of 3 mm, and FIGS. 22C, 22D are corresponding graphs for a pupil diameter of 6 mm.

DETAILED DESCRIPTION OF THE INVENTION

Higher-order monochromatic ocular aberrations manifest themselves as deformed (not plane) wavefronts of light emitted from the eye. These wavefronts can be restored to substantially plane wavefronts by phase compensation over the wavefront surface as one skilled in the art will understand. A higher-order phase compensation element is preferably utilized to provide the desired phase compensation. In a preferred aspect, ocular components or devices having an appropriate phase profile (i.e., surface shape) over at least a portion of a surface of the component or device are provided to correct the higher-order monochromatic aberrations. Such components can include, for example, a deformable mirror, an LCD, a MEMS device, a contact lens, an IOL, an ocular inlay, an ocular onlay, and a reshaped cornea.

Chromatic aberration. on the other hand, is influenced by light amplitude distribution over the pupil area that may or may not have a spectral dependence. A light amplitude modifying clement is utilized to compensate for, or correct, ocular chromatic aberration. In a preferred aspect, a spectral filter or a diffractive optical surface is provided to correct chromatic aberration. More preferably, artificial apodization of the pupil is provided and will be discussed in greater detail below. Artificial apodization can also advantageously be used for improving retinal imaging.

An embodiment of the invention is directed to an optical system for measuring and improving, a person's vision, and includes a higher-order phase compensation element and a light amplitude modifying element. In an aspect of this embodiment, a higher-order phase compensation element is described, with reference to FIG. 1A, by a deformable mirror (DM) 118, used in an adaptive optical system 10 for measuring and correcting wavefront aberrations. The DM (described in more detail below) has a surface that is allowed to deform in shape and thus provide a phase profile which compensates for the aberrated phase profile of the wavefront reflected from the eye. Alternatively, an LCD or a MEMS device (not shown) in place of the DM could provide appropriate phase compensation as a person skilled in the art would appreciate.

Figure 1A:
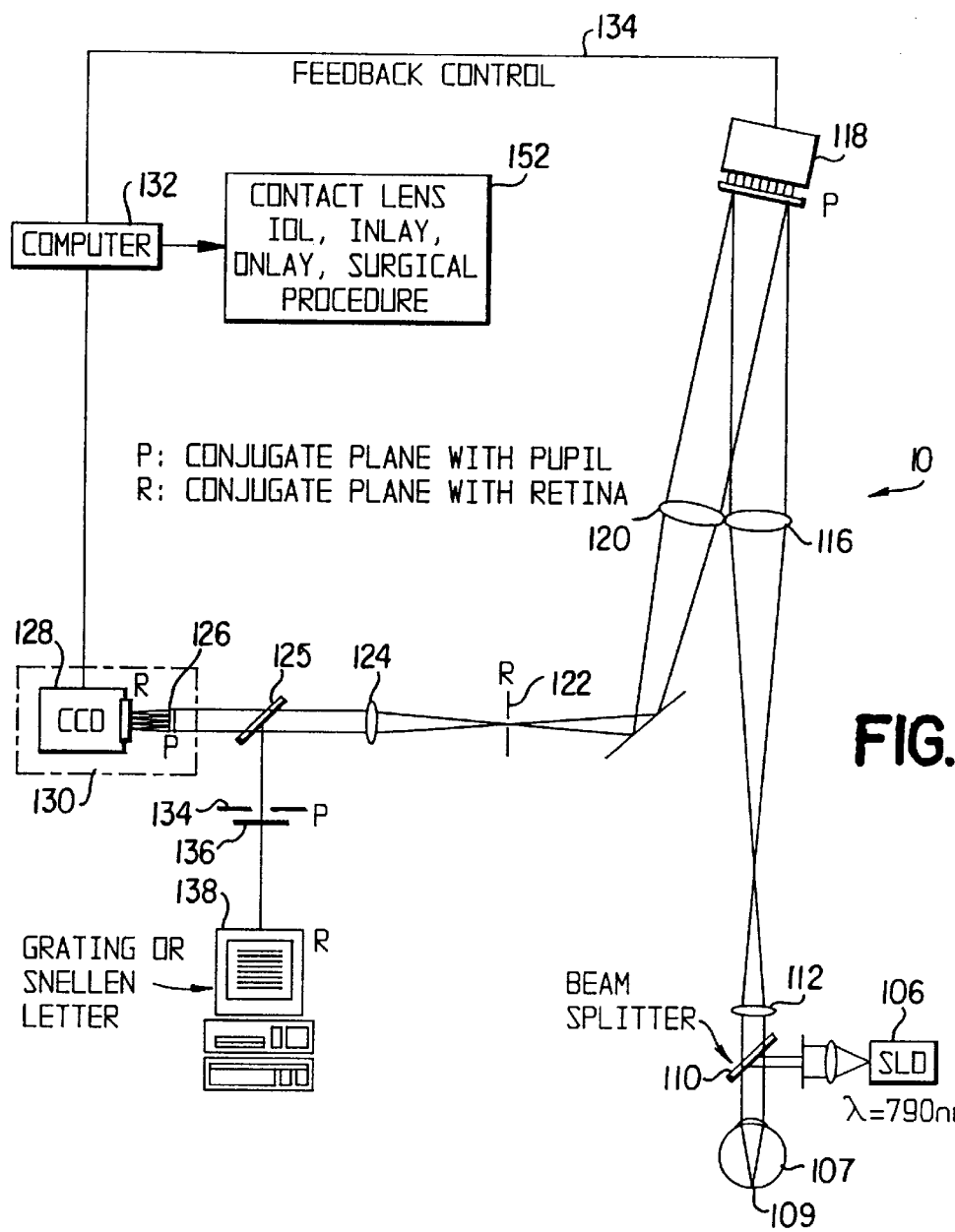
FIGS. 1A and 1B are schematic illustrations of adaptive optical systems for wavefront measurement, aberration correction, psychophysical measurements, and retinal imaging according to the invention.
Figure 2:
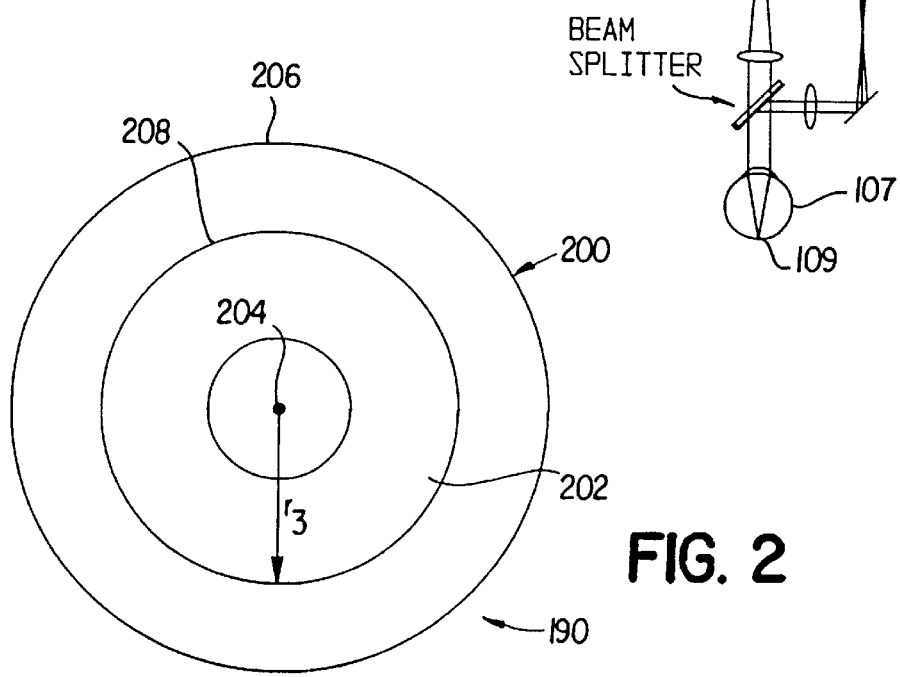
FIG. 2 is a top plan schematic view of an optical system according to an embodiment of the invention.

Referring to FIG. 2. a preferred optical system 190 for correcting a person's vision includes a higher-order phase compensation element in the form of a contact lens 200 (or alternatively, an IOL, (not shown), an ocular inlay (not shown), an ocular onlay (not shown). or a reshaped cornea (not shown)), having a customized surface profile for providing the appropriate higher-order phase compensation. The compensating phase profile can be generated from wavefront sensor data in the form of, e.g., Zernicke coefficient data. This data can be generated by the active optical system 10 shown schematically in FIG. 1A (and described in greater detail below). Final wavefront correction signals from the computer 132 to the DM 118 can also be trans mitted to a lens fabrication system or laser surgical platform 152 where the corrected wavefront aberration data could be used to create the appropriate surface profile on the selected higher-order phase compensation element. Techniques for creating or modifying a surface of a contact lens, an IOL, an inlay, or an onlay are known to those skilled in the art and include, for example, lathing, casting, molding, and laser machining. Refractive surgery or laser photoablation is a preferred technique for appropriately shaping a human cornea.

An exemplary light amplitude modifying element according to an embodiment of the invention is represented by interference filter 136 in FIG. 1A. In a more practical and preferred aspect, light amplitude modification is provided by artificially apodizing a person's pupil via an apodization filter as described below. Apodization herein refers to a non-uniform amplitude transmission of light as a function of pupil radius. Natural apodization in vision is well known in relation to the Stiles-Crawford effect. Due to the waveguide properties of the eye's photoreceptors. the light that enters the periphery of the pupil is less efficient in stimulating the retina than the light that passes through the pupil center. However, the Stiles-Crawford apodization does little to reduce the impact of aberrations on image quality, although theoretically, apodization effectively reduces the pupil diameter and thus reduces the eye's sensitivity to aberrations. Particularly, apodization reduces the height of the side lobes in the point spread function which increases the modulation at the low to mid spatial frequencies. This increases the tolerance for aberrations generally and. as particularly applicable in the instant invention, for defocus and thus for axial chromatic aberration.

Optical properties of a system (e.g., contact lens plus eye) can be summarized by means of a generalized pupil function defined over the exit pupil as $$\rho(r,\theta)=A(r,\theta)\exp[(i2\pi/\lambda)W(r,\theta)] \quad (1)$$

where $A(r,\theta)$ is the amplitude transmitted through the point $(r,\theta)$ of the pupil, and $W(r,\theta)$ is the wave aberration. In a conventional contact lens, $W(r,\theta)$ expresses the higher-order aberrations plus the chromatic defocus for each wavelength. In a customized contact lens for correcting higher-order aberrations, $W(r,\theta)$ expresses the residual monochromatic aberrations plus the chromatic aberration. In both cases, an appropriate filter, $A(r)$, in the contact lens to progressively reduce the transmission of light from the center to the edge of the lens will reduce the impact of the aberrations on the retinal image since the magnitude of aberrations increases with pupil radius. For correcting chromatic aberration the filter should be wavelength dependent, $A(r,\lambda)$, with different attenuation for each wavelength.

Figure 3:
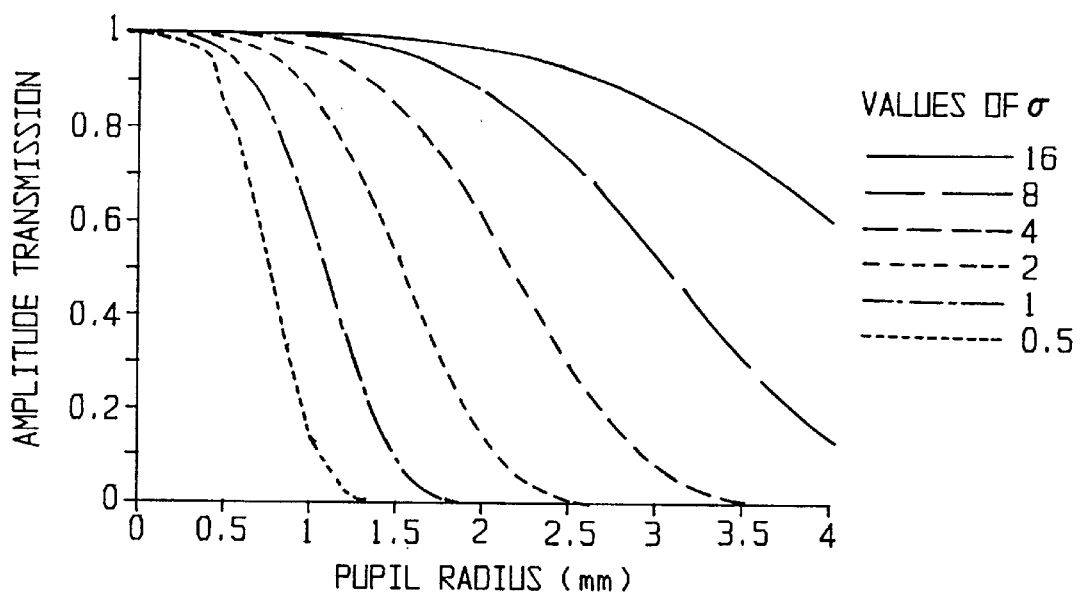
FIG. 3 is a graph of amplitude transmission versus pupil radius for various values of σ (degree of apodization) for an apodization filter according to an embodiment of the invention.
Figure 4:
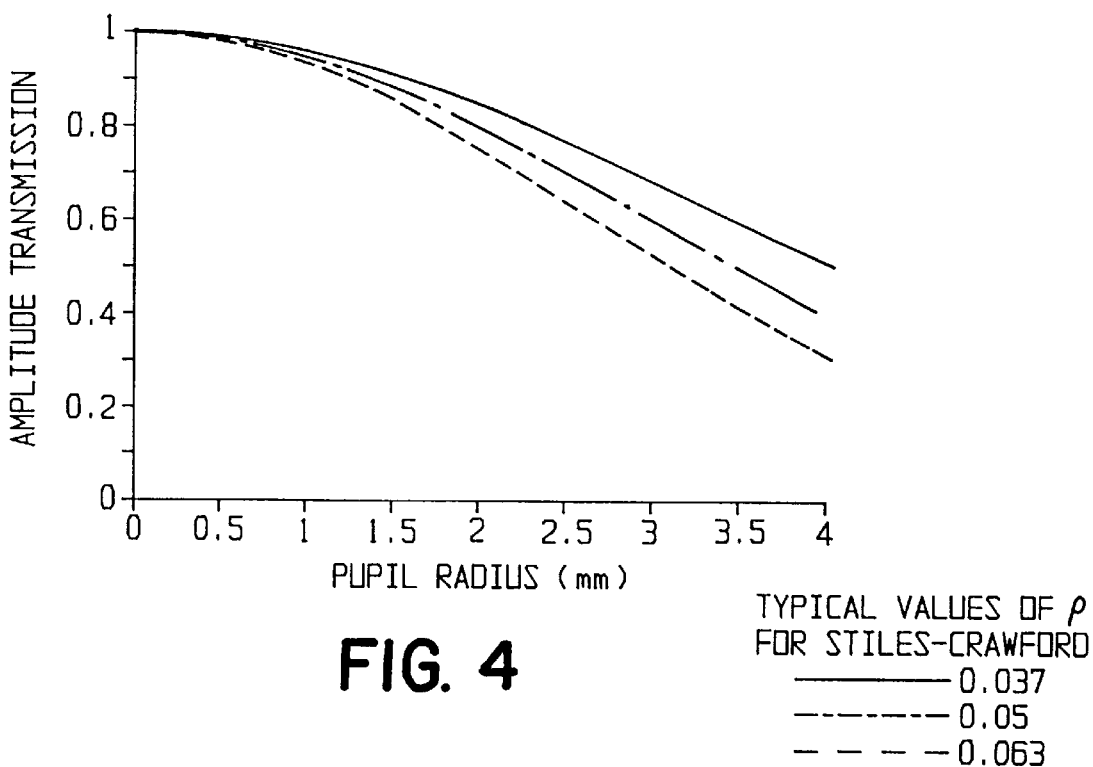
FIG. 4 is a graph of amplitude transmission versus pupil radius under typical conditions of Stiles-Crawford modeling.

Different apodization functions are known to those skilled in the art, with a Gaussian apodization being one of the most common. However, aberrations increase more quickly at the edge of the pupil versus the center and, therefore, other functions characterized by a smooth slope around the center which gets steeper closer to the edge of the pupil will provide the benefits of a Gaussian apodization but with a significant increase in irradiance levels. Accordingly, in a preferred aspect an apodization filter according to the invention is described by a super-Gaussian function as $$A(r)=\exp(-r^4/2\sigma^2) \quad (2)$$

where r is the pupil radius and σ is an apodization parameter relating to the width of the apodization function. FIG. 3 shows the amplitude transmitted by the super-Gaussian transmission function of equation (2) for various pupil radii for different values of the parameter σ. In contrast, FIG. 4 shows the amplitude transmitted for typical values of ρ for the Stiles-Crawford effect as modeled by the Gaussian function $$A(r)=\exp(-\rho \ln 10 \cdot r^2/2).$$

Exemplary apodization filters according to the invention are described below.

Exemplary Filter No. 1

Figure 7:
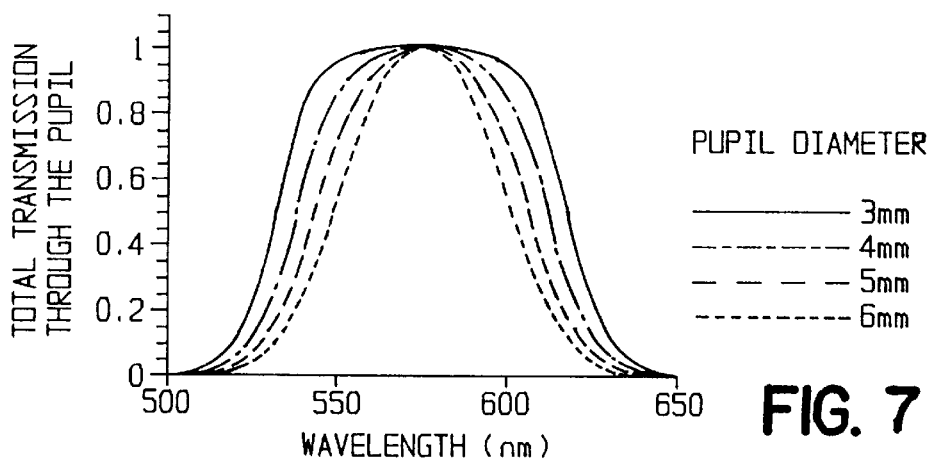
FIG. 7 is a light transmission curve for various pupil diameters in accordance with an embodiment of the invention.
Figure 5:
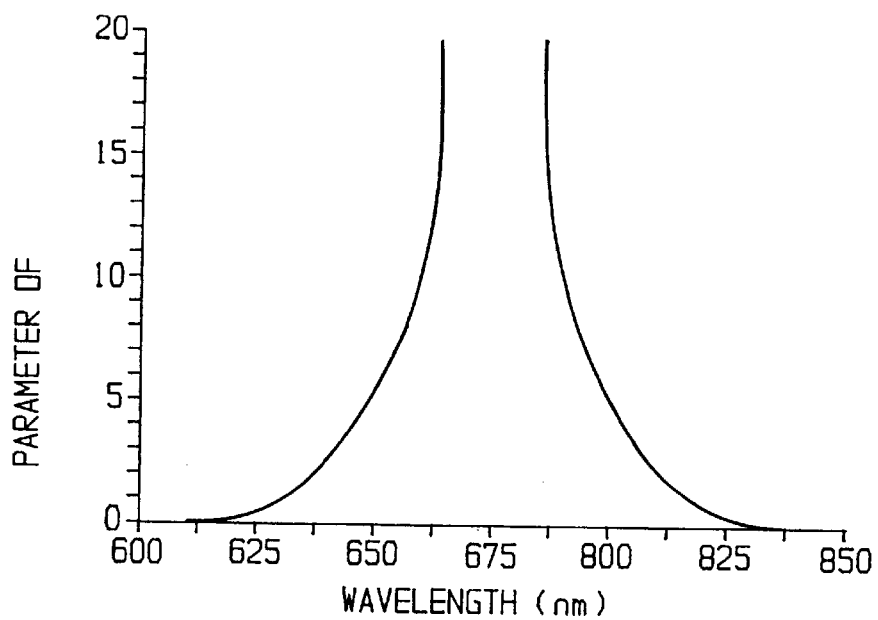
FIG. 5 is a spectral profile curve according to an embodiment of the invention.
Figure 6:
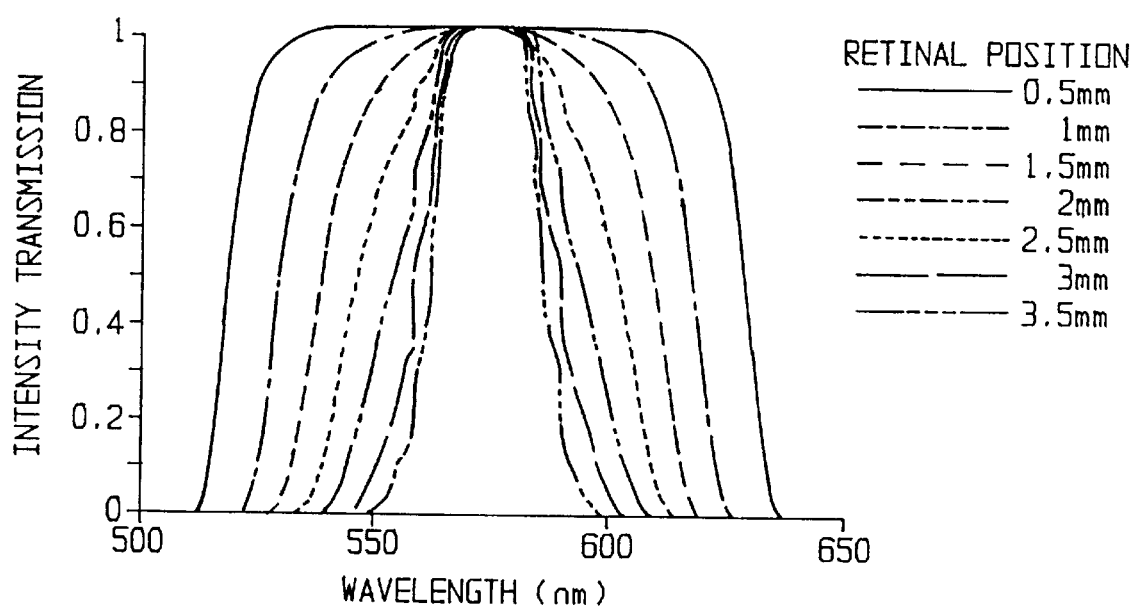
FIG. 6 is a spectral profile curve according to an embodiment of the invention as a function of wavelength for different radial positions for each wavelength.

Referring to FIG. 5, the values of the parameter σ(λ) over a portion of the visible wavelength spectrum are shown for a first exemplary apodization filter according to the invention. In this case, no apodization is made within an interval of 20 nm centered at the reference wavelength of 575 nm. FIG. 6 shows the value of the light intensity transmitted with this filter through different pupil radii for each wavelength. FIG. 7 shows the total transmission through the entire pupil aperture for every wavelength. Although a particular spectral bandwidth is illustrated, it will be appreciated that the particular spectral transmission region will be selected based upon the desired application. For instance if increased night vision is desired, the spectral transmission bandwidth could be shifted to better coincide with the rod visual sensitivity of the eye.

Figure 8:
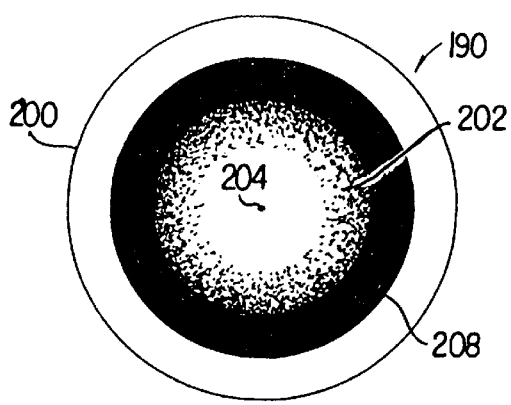
FIG. 8 is a diagrammatic illustration of an apodization filter according to an embodiment of the invention.

An exemplary optical device 190 in the form of an artificially apodized custom contact lens according to an embodiment of the invention is schematically shown in FIG. 2 and FIG. 8. The contact lens 200 has an optical zone defined by $r_3$, and provides correction of the higher-order monochromatic aberrations as discussed above. An apodizing filter 202 according to Exemplary Filter No. 1 as shown in FIG. 8 is aligned with the center 204 of the lens 200 along an optical axis (not shown) of the lens. Wavelength dependent apodization can be achieved by introducing a color absorbing material, such as a dye, across the optical zone of the contact lens 200 which provides increasing density from the center 204 to the edge 208 of the optical portion of the lens. It will be appreciated by those skilled in the art that various methods exist for creating such a filtering profile. For example contact lens material initially provided in cylindrical bar form can be immersed in an appropriate dye that diffuses into the lens material. Desired density profiles can be achieved by appropriate diffusion times and control of other known parameters.

Exemplary Filter No. 2

Figure 9:
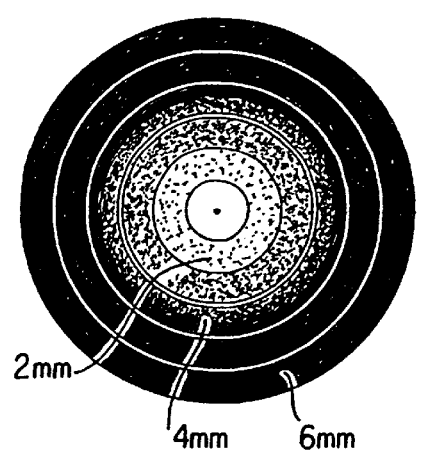
FIG. 9 is a schematic diagram of another apodization filter embodiment according to the invention.

In an alternative aspect of the apodizing filter as diagrammatically illustrated in FIG. 9, appropriate filter material is deposited in concentric annular rings 220, 221, 222, etc. over the lens surface. In this aspect, the filtering material provides a band pass filter in each ring, each ring having a narrower bandwidth as the distance to the center of the lens increases. For example, from lens center (r=0) to r=0.5 mm there is no filter; from 0.5 to 1 mm the filter could have a spectral profile according to that shown in FIG. 6 for that particular radial position, and similarly for various radii out to the edge of the lens. different annular radii and filter profiles depending upon application are well within the scope of this aspect of the invention.

Exemplary Filter No. 3

Figure 10:
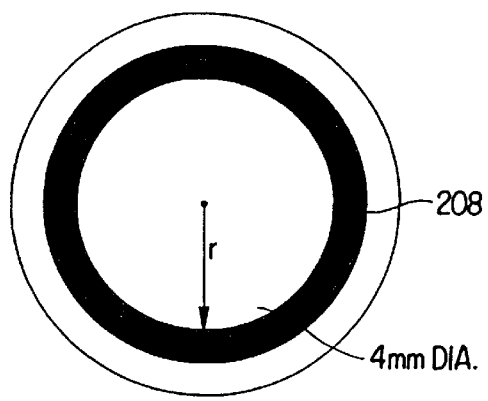
FIG. 10 is a diagrammatic illustration of an apodization filter according to an aspect of the invention.

Referring to FIG. 10, the simplest case for the filter embodiment of Example Filter No. 2 above is the use of a single ring. As illustrated, filtering begins at r=2 mm and continues to the edge 208 of the optical portion of the lens to avoid the entrance of the short and long wavelengths through the pupil larger than 4 mm diameter. Preferably, the filter will comprise a pass band filter with a bandwidth λ=[550–610 nm]. As described above, other radii and bandwidths may be applicable.

Exemplary Filter No. 4

Figure 11:
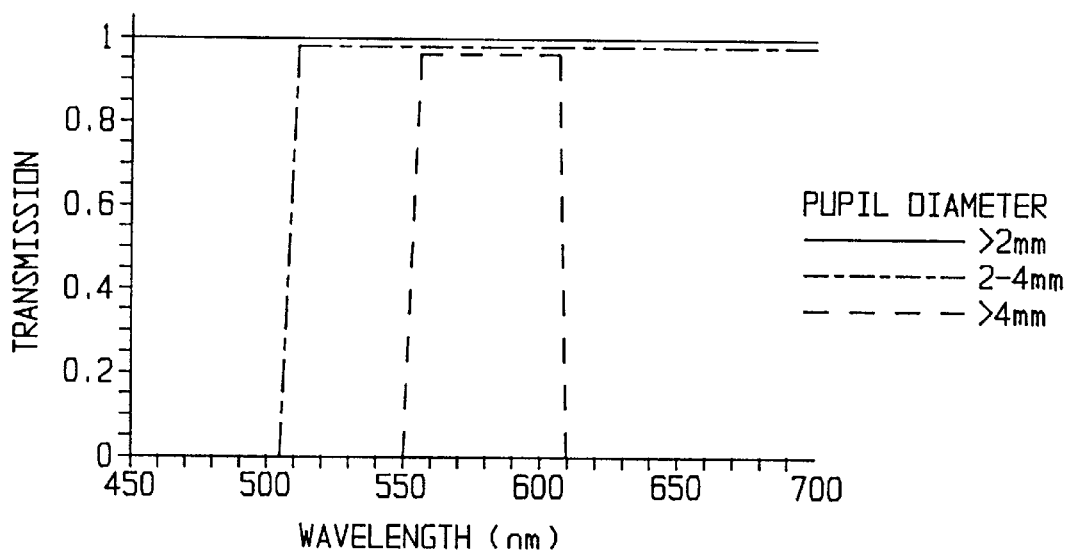
FIG. 11 is a transmission curve for an apodization filter embodiment according to the invention.

In an alternative aspect of this embodiment of the invention, the contact lens 200 illustrated in FIG. 2 could incorporate two filters in two different zones of the contact lens; e.g., no filter in the central 2 mm diameter of the lens, a long pass filter (λ>510 nm) in the zone between 2 and 4 mm diameter, and a pass band filter for λ=[550–610] nm for diameters larger than 4 mm. The transmission function for this filter is illustrated in FIG. 11.

Exemplary Filter No. 5

Figure 12:
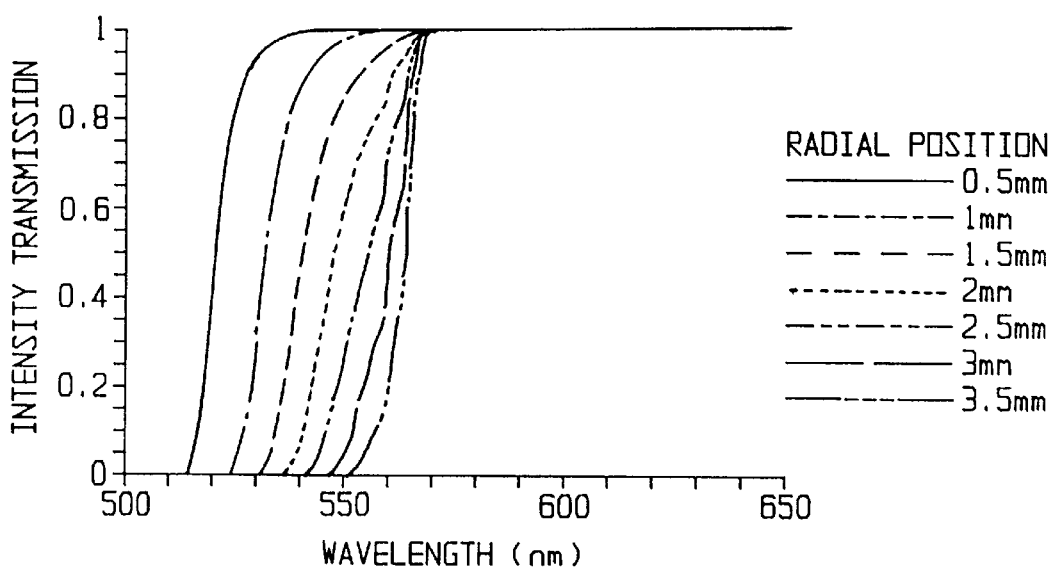
FIG. 12 is a filter transmission curve of a long-pass filter embodiment according to the invention.

In an alternative embodiment, the apodization may take the form of a long-pass filter in contrast to the band pass filters described above, for eliminating only the wavelengths below the reference wavelength. FIG. 12 illustrates this alternative for Exemplary Filter No. 1.

Figure 13A:
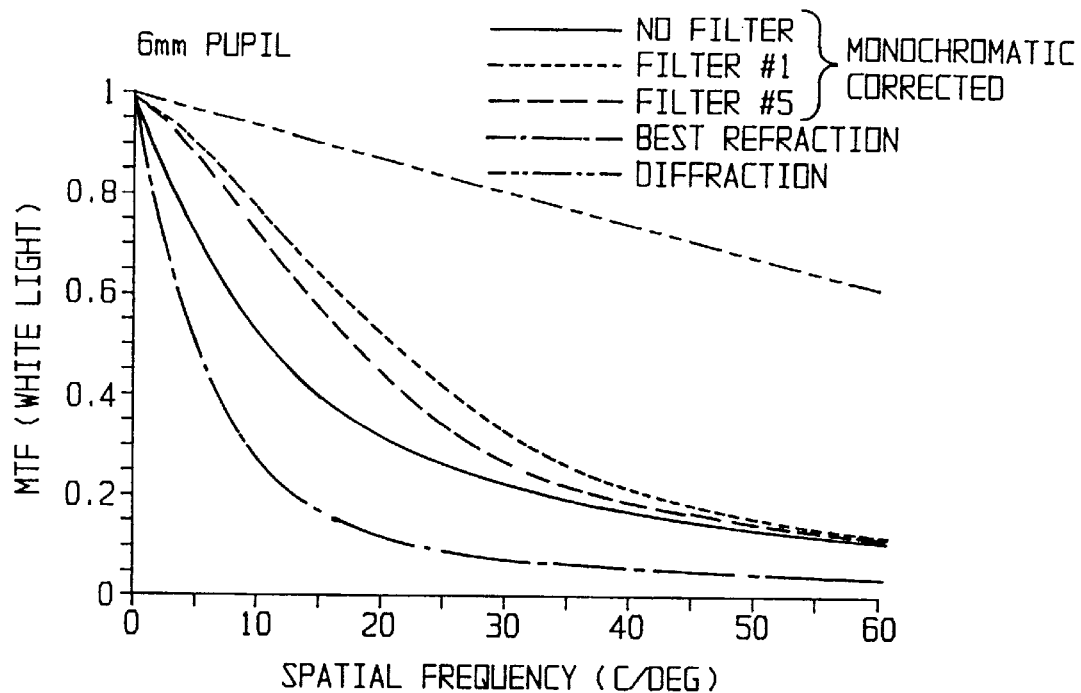
FIGS. 13A, 13B are MTF graphs showing the effects of different apodization filter embodiments according, to the invention.
Figure 13B:
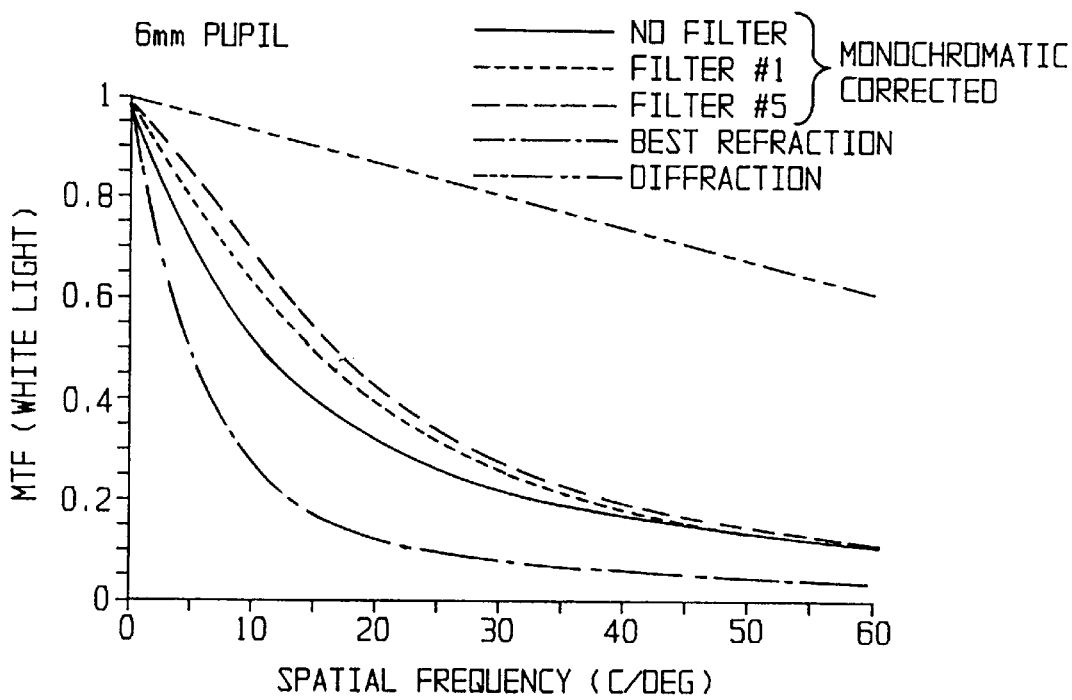

FIGS. 13A, 13B show the white light MTFs corresponding to an optical element (e.g., a contact lens) that corrects the higher-order monochromatic aberrations and which incorporates Example Filters 1 and 5 and Example Filters 3 and 4, respectively, for correcting chromatic aberration. All data are presented with respect to a 6 mm artificial pupil diameter.

Figure 14:
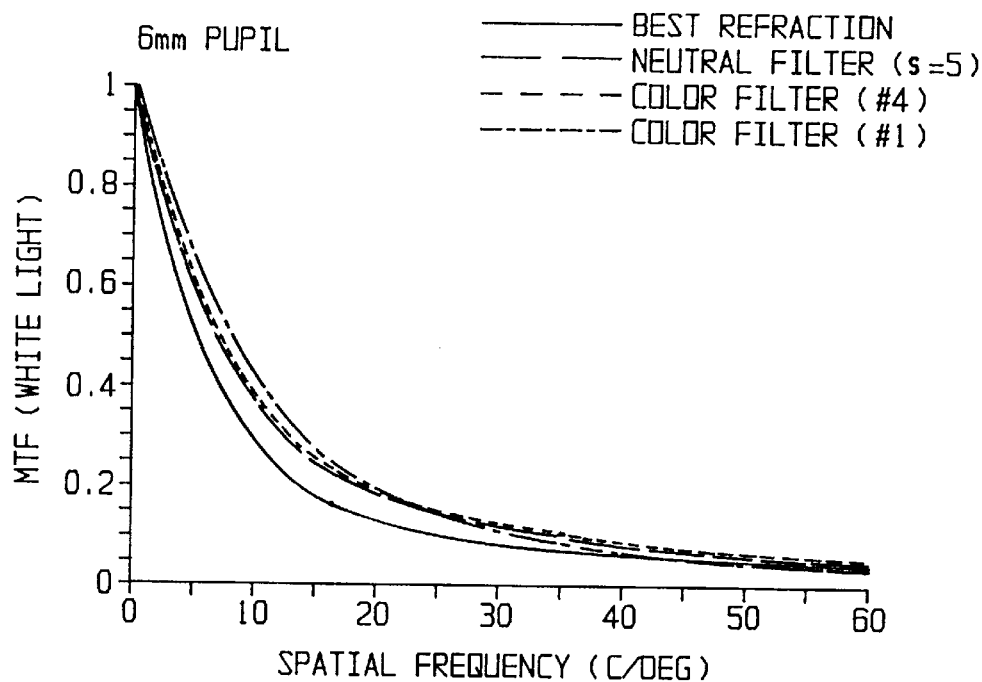
FIG. 14 is an MTF graph of different filter embodiments according to the invention.

FIG. 14 shows the white light MTFs for different apodization filters according to the invention when neither the monochromatic nor the chromatic aberrations were corrected. In this case, the visual benefit is similar to that obtained with a simple stop of 4 mm diameter centered on the contact lens. As can be seen, the results are inferior to the results shown in FIGS. 13A, 13B.

Figure 15:
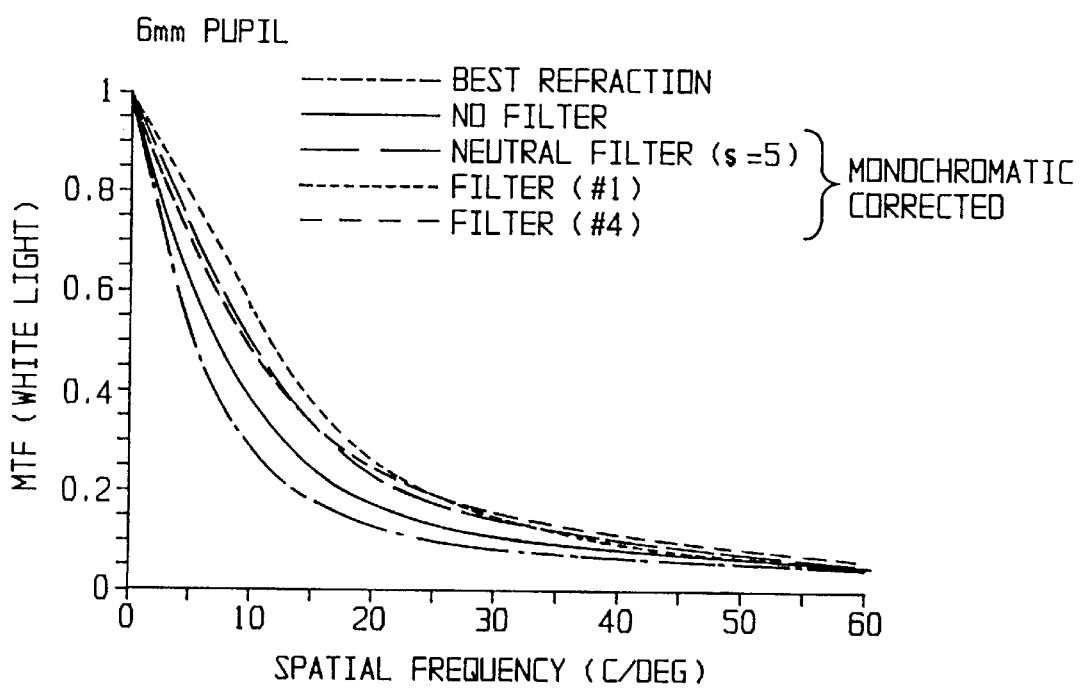
FIG. 15 is an MTF graph with coma and spherical aberration corrected in combination with an apodizing filter according to an embodiment of the invention.

FIG. 15 shows the benefit of correcting coma and spherical aberration with a customized contact lens, and the additional benefit when the lens incorporates a filter for correcting chromatic aberration according to the invention. This graph illustrates that a visual benefit can be obtained even when only some of the higher-order monochromatic aberrations are corrected in addition to correcting chromatic aberration.

In a preferred embodiment, the optical system for improving a person's vision could include the higher-order phase compensation element and the light amplitude modifying element being resident in a common optical component or substrate. The optical system 190 of FIG. 2 and FIG. 8 illustrates such a system. This type of integrated system is preferred when the higher-order phase compensation element is either a contact tens, an IOL, an inlay, or an onlay, but not a reshaped cornea. The light amplitude modifying element can advantageously be one of the apodization filters described above.

In an alternative embodiment, the optical system for improving a person's vision could include the higher-order phase compensation element and the light amplitude modifying element being resident in separate optical components (not shown). This system can include one or more of the higher-order phase compensation elements described above in combination with an apodized or filtered spectacle lens, for example, used in conjunction with the higher-order phase compensation element. Preferably, the separated platform optical system would be utilized when the higher-order phase compensation element is a reshaped cornea.

Figure 1B:
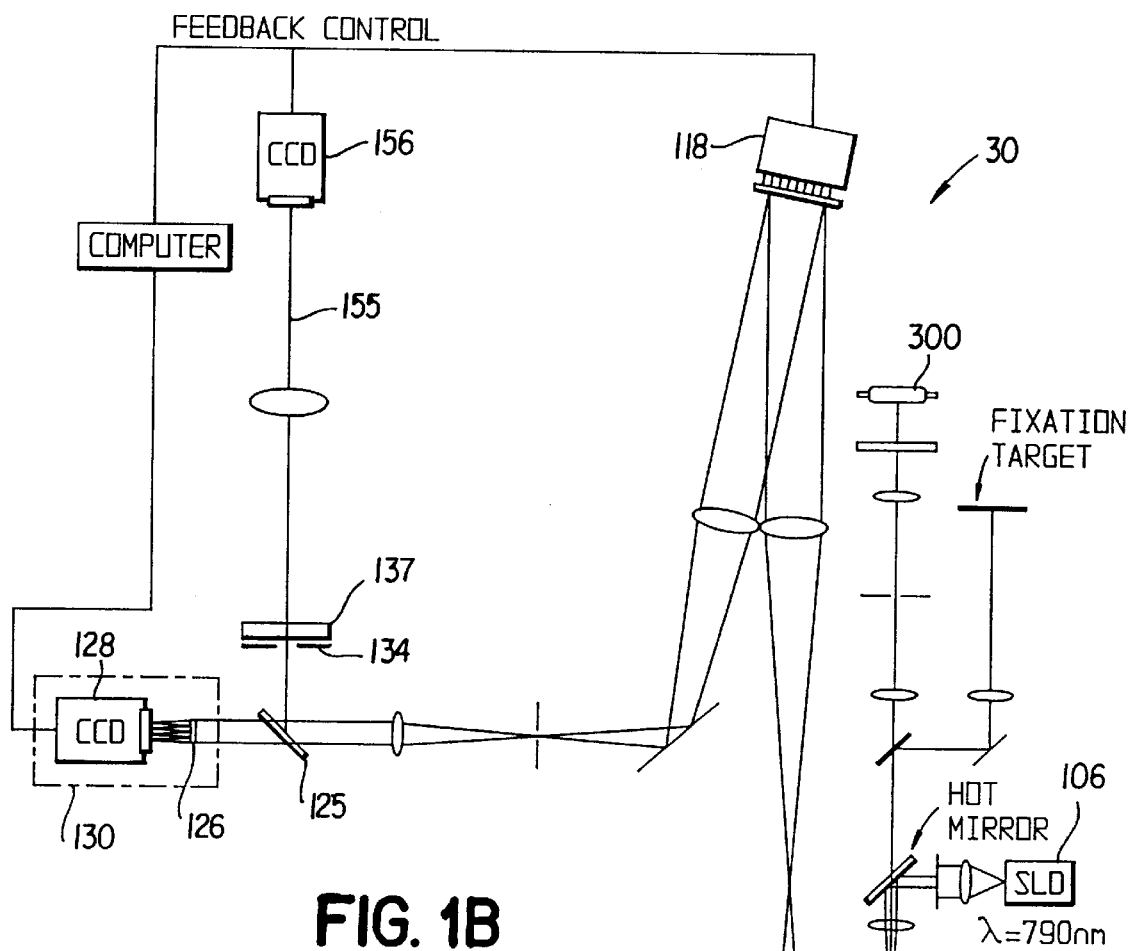
Figures 16, 21:
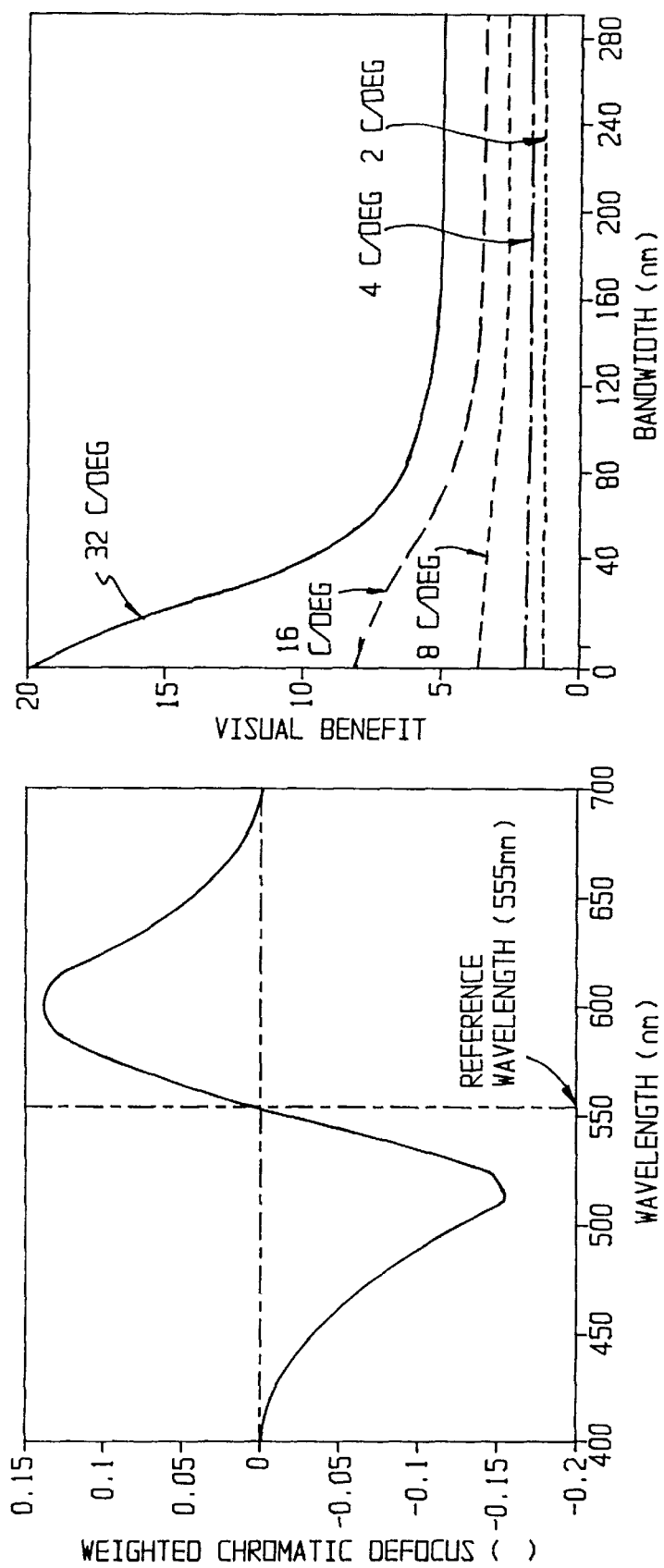
FIG. 16 is a graph of weighted chromatic defocus as a function of wavelength centered at a reference wavelength of 555 nm.
FIG. 21 is a graph of visual benefit for different spatial frequencies as a function of wavelength bandwidth.

Another embodiment of the invention relates to high resolution retinal imaging and providing a subject with supernormal retinal image quality. FIG. 1B schematically illustrates a retinal imaging system 30 that can be used to provide a subject with supernormal retinal image quality and which also can be used to provide high resolution images of the retina 109 of an eye 107. The optical system 30 is substantially similar to the optical system 10 of FIG. 1A with the notable exceptions of a broadband light source 300 for illuminating the retina 109. and optical path 155 leading to a second CCD camera 156 for capturing the retinal image. In this embodiment, the broadband retinal illumination is provided by a Krypton flash lamp 300. The Krypton flash lamp 300 is imaged onto the eye's pupil, typically in a 4 msec flash. thereby illuminating a retinal disk on the retina 109 that is preferably one degree in diameter. The image of the retina 109 is reflected by the deformable mirror 118 which has already been shaped to compensate for the eye's higher-order monochromatic aberrations as described herein with respect to FIG. 1A. The light is reflected by the mirror 125 through an artificial pupil 134 which is immediately followed by an apodizing filter 137. and is then focused onto the retinal imaging CCD 156. An improved retinal image (and corresponding retinal imaging ability of the subject) can be obtained over the improved retinal image quality discussed in Williams et al. U.S. Pat. No. 5,777,719 due to correction of chromatic aberration provided by the apodizing filter 137. The apodizing filer 137 preferably is described by any of the exemplary apodization filters discussed above. It will be appreciated by a person skilled in the art that such a filter can be provided, for example, by printing the desired filter profile on a suitable substrate for incorporation into the optical system 30. Although an apodization filter as described above is a preferable device for correcting chromatic aberration in the retinal imaging system of FIG. 1B, other filters such as neutral density filters and interference filters, for example, could be used. We observed, however, that merely narrowing the bandwidth to some portion of the full visible bandwidth to reduce chromatic aberration had the disadvantage of reducing total luminance. FIG. 21 illustrates this effect from the perspective of visual benefit. Narrowing the bandwidth to 50 nm (530 mn to 580 mn) provided a 2x visual benefit over that obtained over the full visible bandwidth (290 nm), however, the luminance was reduced by approximately 50% with an accompanying loss of color vision.

In conjunction with the optical components, devices and systems described above, an embodiment of the invention is directed to a method for improving a person's vision. The method includes correcting an ocular higher-order monochromatic aberration and correcting ocular chromatic aberration, preferably and substantially axial chromatic aberration.

Higher-order monochromatic aberration data was obtained from a number of subjects using an adaptive optical system 10 schematically shown in FIG. 1A. The device shares many features with the adaptive optical system illustrated and described in Williams U.S Pat. No. 5,777,719, the disclosure of which is incorporated by reference herein in its entirety, and in FIG. 1B. In order to obtain aberration data, a subject's pupil was dilated with mydriacyl (1%) or cyclogyl (1%). The subject's head position was then stabilized in the system 10 with a bite bar (not shown) to locate the position of the subject's eye 107. A super luminescent diode 106 emitting at 790 nm was collimated and reflected by a beam splitter 110 to a point source on the retina 109 of eye 107. Light reflected from the retina passes through the beam splitter 110 and is directed through lenses 112 and 116 onto deformable mirror 118 that is located in a conjugate plane with the eye's pupil. The deformable mirror 118 (Xineticx, Inc.) included 37 lead magnesium niobate (PMN) actuators to shape the mirror's surface and correct the higher-order monochromatic aberrations. light reflected from the deformable mirror 118 is focused by lens 120 in a location coincident with aperture 122 that is located conjugate to the retina 109. The light is then collimated by lens 124 and passes through partially transmitting mirror 125 to a lenslet array 126 of a Hartmann Shack wavefront sensor 130. The Hartmann Shack wavefront sensor 130 included a square array of 221 lenslets (focal length=24 mm, inter-lens spacing 0.4 mm; available from Adaptive Optical Associates) and provided wave aberration data up to tenth radial order (63 Zernicke coefficients excluding piston, tip, and tilt). The lenslet array 126, located in a conjugate plane of the eye's pupil, forms an aerial image of the retinal point source on a CCD camera 128 located in a conjugate plane with the retina 109. Wavefront data from the wavefront sensor 130 is processed by computer 132 and is directed to the deformable mirror 118 through a feedback control loop 134. As further shown in FIG. 1A, a Mitsubishi Diamond Pro 710 CRT 138 was located in a conjugate plane with the retina 109 and was used to display a visual stimulus to the eye in the form of a grating or a particularly oriented alphabetic letter for measurement and evaluation of contrast sensitivity and visual acuity. The screen of the CRT appeared white with a broadband, bimodal emission spectrum. The display was viewed through the 6 mm pupil 134 providing a visual angle of one degree. Retinal illuminance was set at 57 Td. A neutral density filter was used as necessary to equalize illuminance levels. A narrow bandwidth interference filter 136 having a 10 nm bandwidth (FWHM) about a center wavelength of 550 nm was used in some of the measurements to correct chromatic aberration. In other measurements, longitudinal chromatic aberration was corrected with an achromatizing lens as described in Bedford and Wyszecki, J. Opt. Soc. Am. 47, 564–565 (1957). It has been shown in the prior art that longitudinal chromatic aberration is about two diopters (D) over the visible spectrum. The amount of chromatic defocus is larger (−1.5 D) at shorter wavelengths (400 nm) than the chromatic defocus (0.5 D) at longer wavelengths (700 nm). However. the perceived chromatic defocus is nearly symmetric about the reference wavelength of 555 nm, as shown in FIG. 16, when considered in connection with human photopic spectral sensitivity. Chromatic aberration could also have been measured as a person skilled in the art would appreciate.

For measuring contrast sensitivity the subject fixated on a 16 c/deg grating and defocus was corrected with a Badal Optometer while astigmatism was corrected with a trial lens when necessary. Six different spatial frequencies of 2, 4, 8, 16, 24 and 32 c/deg were presented in random order to the subject. Five measurements were made for each spatial frequency. Contrast threshold was determined using the well known adjustment method.

To measure visual acuity, each of the capitalized letter EI. with four different orientations was displayed on the CRT 138 in random order at 100% contrast. Defocus and astigmatism were corrected as necessary. Subjects respond to the orientation of the letter and acuity was measured at the line thickness of the letter for which 50% of responses were correct. Four measurements were made in monochromatic and white light with two different retinal illuminance levels, 57 Td and 575 Td, with a 6 mm pupil.

Psycho-physical Visual Benefit

FIGS. 17A and 17B. respectively, show the contrast sensitivity functions for two subjects (YY,GYY) with (a) defocus and astigmatism only corrected; (b) after correction of the higher-order monochromatic aberrations as well as defocus and astigmatism; and (c) after correcting both monochromatic aberrations and chromatic aberration. The results are similar for both subjects. As shown, the contrast sensitivity obtained by correcting the higher-order monochromatic aberrations is measurably higher than when defocus and astigmatism alone were corrected. This comparison illustrates that higher-order monochromatic aberrations in normal eyes reduce visual performance. Moreover, an even larger increase in contrast sensitivity was obtained, as shown, by correcting both chromatic and the higher-order monochromatic aberrations. The contrast sensitivity functions illustrated in FIGS. 17A, 17B show that chromatic aberration has the strongest dilutive influence on the benefit of correcting the higher-order monochromatic aberrations.

Figure 18B:
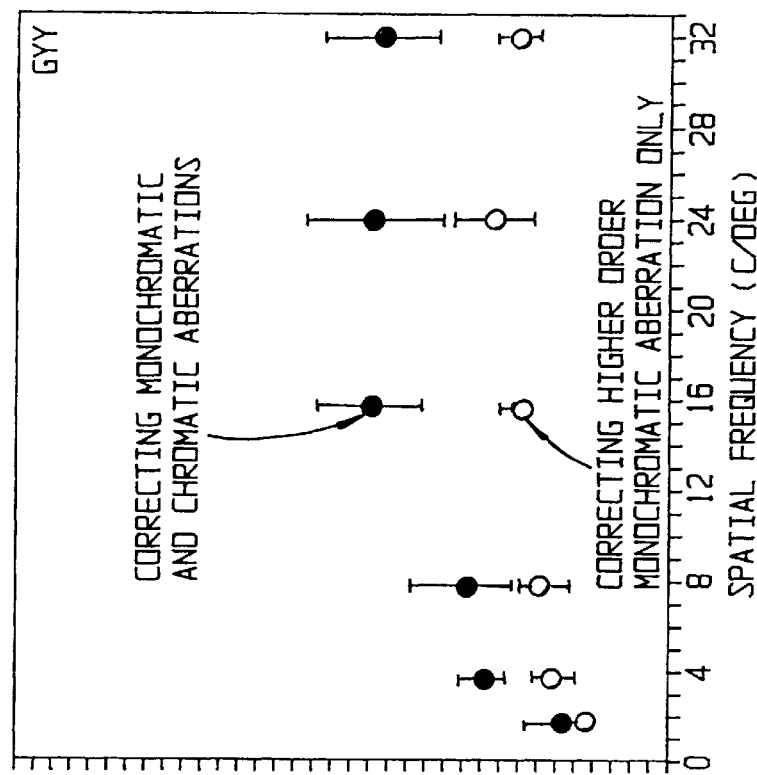
FIGS. 18A, 18B are graphs of visual benefit versus spatial frequency before and after aberration correction according to an embodiment of the invention.
Figure 18A:
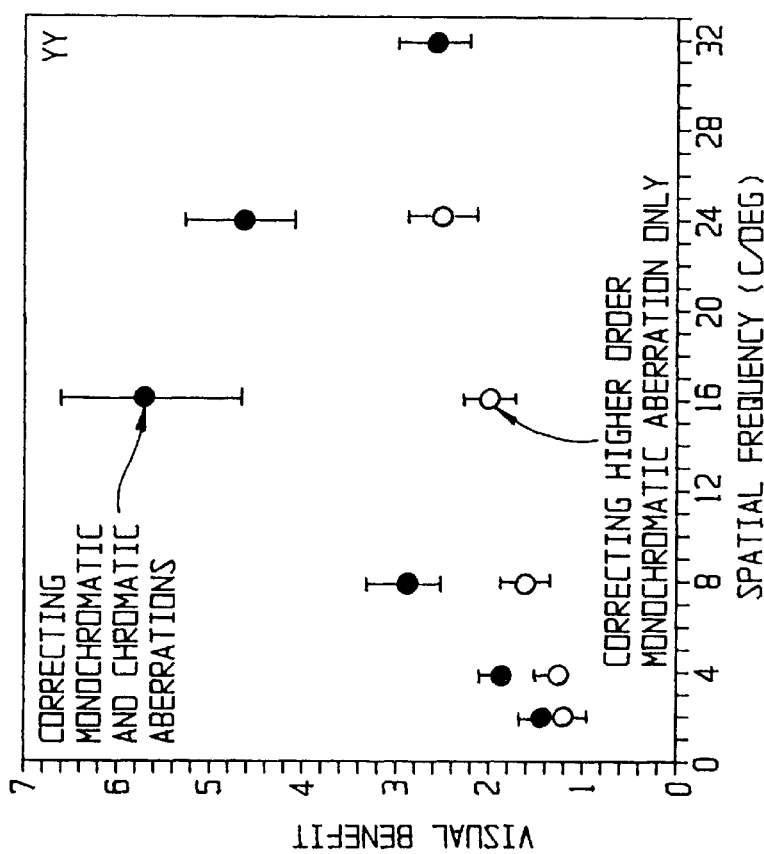

FIGS. 18A. 18B show the psycho-physical visual be befit, $VB_{psy}$, from correcting chromatic and the higher-order monochromatic aberrations over the $VB_{psy}$ from correcting the higher-order monochromatic aberrations alone, for the two subjects referred to in FIGS. 17A and 17B respectively. The visual benefit due to correcting the higher-order monochromatic aberrations only (open circles) is improved by a factor of two on average at 16 c/deg and 24 c/deg. or the two subjects, respectively. The maximum visual benefits are approximately a factor of five for YY and 3.2 for GYY at 16 c/deg when both the monochromatic aberrations and chromatic aberration were corrected (filled circles). The above measurements were made with a 6 mm diameter pupil size at a retinal illuminance of 57 Td.

Figures 19A, 19B:
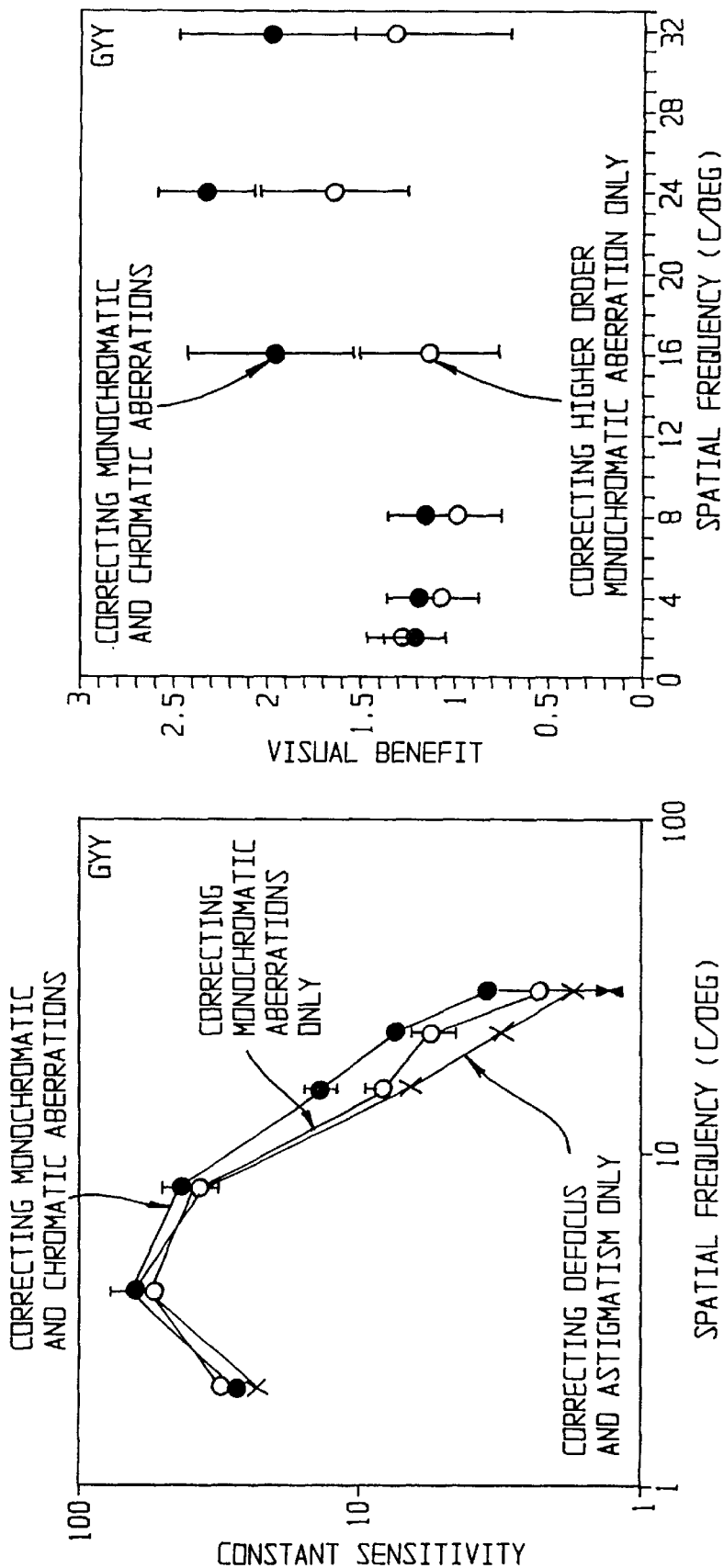
FIGS. 19A, 19B are graphs of contrast sensitivity and visual benefit, respectively, for a 3 mm pupil diameter, for various aberration corrections according to an embodiment of the invention.

In contrast, FIGS. 19A, 19B show measured data for contrast sensitivity and $VB_{psy}$, respectively, for subject GYY with a pupil diameter of 3 mm. It can be seen that a modest benefit of correcting higher-order aberrations or/and chromatic aberration occurs at the higher spatial frequencies, corresponding to a factor of two at 16 c/deg in white light. The visual benefit of either correcting the higher-order monochromatic aberrations only or correcting both chromatic and monochromatic aberrations is smaller than for a 6 mm pupil diameter.

Figures 20A, 20B:
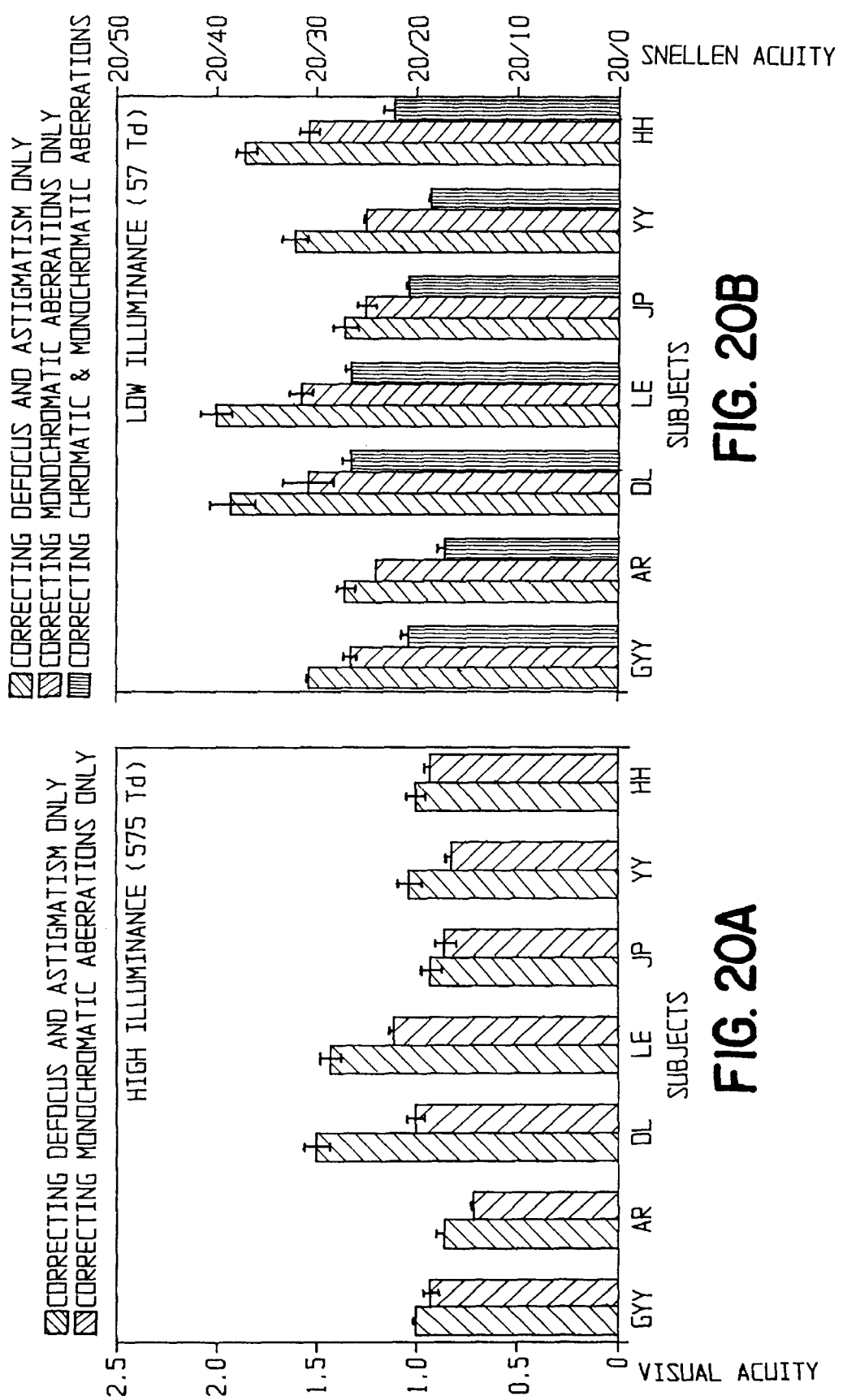
FIGS. 20A, 20B are graphs of visual acuity for several subjects, for various aberration corrections, at different luminance levels for a 6 mm pupil diameter.

FIGS. 20A. 20B show visual acuity measurements at high (575 Td) and low (57 Td) retinal illuminance levels, respectively, for seven subjects. Prior to obtaining this measurement. defocus and astigmatism were Subjectively corrected with a trial lens as necessary. The figures illustrate that correcting only monochromatic aberrations provides an average increase for the seven subjects by a factor of 1.2 at 575 Td and 1.4 at 57 Td. Correcting both aberrations in combination improved visual acuity by a factor of 1.6 as shown in FIG. 20B. Thus, this further supports the observation that visual acuity as well as contrast sensitivity benefit from correcting higher-order monochromatic aberrations and, in addition. that increased benefits are realized by also correcting chromatic aberration.

Optical Visual Benefit

FIGS. 22A and 22B. respectively, show the averaged MTFs and the calculated $VB_{opt}$ based on the wave aberration measurements of 17 subjects, at a 3 mm pupil diameter. Likewise, FIGS. 22C and 22D show similar information for a 6 mm pupil. The calculations assumed a perfect correction such that there was no effect of monochromatic aberrations and/or chromatic aberration after correction. The optical modulation transfer function in monochromatic light was calculated from the subjects' wave aberration data as measured with the active optical system of FIG. 1A. The white light MTF was obtained by summing each monochromatic MTF defocused by longitudinal chromatic aberration, displaced by transverse chromatic aberration, and weighted by the photopic spectral sensitivity of the eye at each wavelength. The foveal transverse chromatic aberration value measured by Thibos et al., Vision Research, 30, 33–49

(1990) was used. The monochromatic MTFs were computed every 10 nm from 405 nm to 695 nm assuming, an equally distributed energy spectrum. The reference wavelength free of chromatic aberration was 555 nm coincident with the maximum photopic sensitivity. Prior to correcting the aberrations, the eye's best focus for the gratings is different for different spatial frequencies in both monochromatic and white light. We chose an amount of defocus to maximize the modulation transfer function of a 16 c/deg grating.

As shown in the Figures, there is almost no optical visual benefit from only correcting chromatic aberration for a 3 mm pupil. A three-fold increase in contrast sensitivity can be seen when only the higher-order monochromatic aberrations were corrected at 32 c/deg. In contrast, with reference to FIGS. 22C and 22D, correction of only the higher-order monochromatic aberrations provided a 5× larger optical visual benefit at middle and higher spatial frequencies for a 6 mm pupil. However, the calculated optical visual benefit from correcting both chromatic and the monochromatic aberrations is substantially larger than that from correcting higher-order monochromatic aberrations only. The theoretical visual benefits are larger than the empirical data presented in FIGS. 19A. 19B, 20A and 20B because the adaptive optics system was incapable of perfect correction. Theoretical calculations indicate that correcting both the higher-order monochromatic aberrations and chromatic aberration over a large pupil diameter could increase optical quality on the retina by a factor approaching 20 at 32 c/deg. When either the monochromatic aberration or the longitudinal aberration alone is corrected. the uncorrected aberration dilutes the benefit of correcting the other.

An aspect of the method embodiment according to the invention is directed to providing the higher-order monochromatic aberration correction and the chromatic aberration correction in a common optical component. For example, any of a contact lens, an IOL. an inlay or an onlay, providing phase compensation, could be artificially apodized to correct chromatic aberration.

In an alternative aspect, the higher-order monochromatic aberration correction and the chromatic aberration correction could be provided in separate optical components. For example, any of a contact lens, an IOL, an inlay. an onlay, or a reshaped cornea could provide phase compensation and an apodized or filtered spectacle lens could provide chromatic correction.

The invention thus demonstrates. among other things, that visual benefit is improved by correcting higher-order monochromatic aberrations of the eye, and that an even greater visual benefit is obtained when chromatic aberration is corrected in addition to the higher-order monochromatic aberrations. Practical devices and methods have been described for improving a person's vision. The measured improvement in vision described above is in good agreement with theoretical values of visual benefit and contrast sensitivity for perfect correction.

Figure 23:
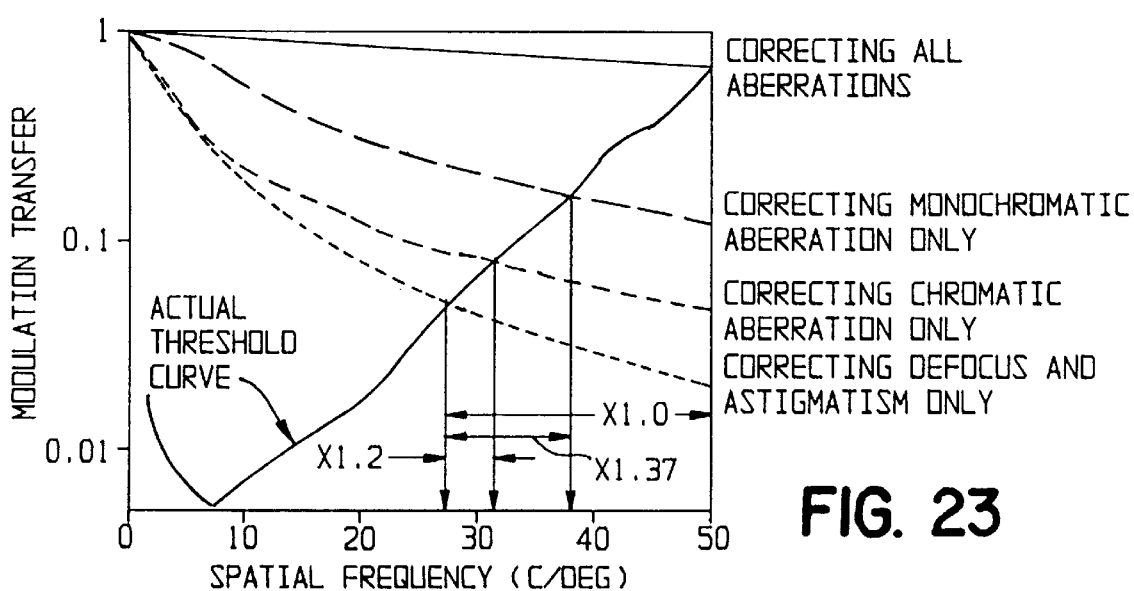
FIG. 23 is a graph of MTF as a function of spatial frequency in conjunction with the neural threshold curve illustrating the theoretical increase in visual acuity according to an embodiment of the invention.

FIG. 23 shows the theoretical increase in visual acuity by correcting higher-order monochromatic aberrations or/and chromatic aberration for a 6 mm pupil. Intersections of MTFs and the neural threshold curve (as measured by Green. J. Physiol. 190, 583–593 (1967) predict visual acuity. The multiplicative numbers in FIG. 23 correspond to benefits in visual acuity that could be achieved by correcting various aberrations.

In summary, the invention relates to methods and devices for improving a person's vision by correcting, in combination, higher-order monochromatic ocular aberrations and chromatic aberration. In addition, the invention relates to a system for improved retinal imaging.

Notwithstanding, the preferred embodiments specifically illustrated and described herein, it will be appreciated that various modifications and variations of the instant invention are possible in light of the description set forth above and the appended claims, without departing from the spirit and scope of the invention.

We claim:

1. A method for improving a person's vision, comprising:
   correcting an ocular higher-order monochromatic aberration of the person's vision; and
   correcting an ocular chromatic aberration of the person's vision.

2. The method of claim 1, wherein the ocular higher-order monochromatic aberration comprises third and higher-order radial Zernicke modes.

3. The method of claim 2, wherein the ocular higher-order monochromatic wave aberration comprises fifth to tenth-order radial Zernicke modes.

4. The method of claim 1, further comprising correcting defocus and astigmatism of the person's vision.

5. The method of claim 1, wherein correcting the ocular higher-order monochromatic aberration comprises measuring the ocular wave aberration represented by third and higher-order radial Zernicke modes.

6. The method of claim 5, wherein correcting the ocular higher-order monochromatic aberration comprises measuring the ocular wave aberration represented by fifth to tenth-order radial Zernicke modes.

7. The method of claim 1, wherein correcting the ocular higher-order monochromatic aberration comprises providing an ocular device having a phase profile suitably adapted to correct said aberration.

8. The method of claim 7, wherein said ocular device comprises at least one of a contact lens, an IOL, an ocular inlay and an ocular onlay.

9. The method of claim 1, wherein the step of correcting an ocular higher-order monochromatic aberration comprises surgically altering a characteristic of the person's eye to correct said ocular higher-order monochromatic aberration.

10. The method of claim 1, wherein the step of correcting ocular chromatic aberration comprises attenuating a spectral bandwidth of light incident on a person's eye, said bandwidth being in the range from about 10 nm to 150 nm over the visible spectrum.

11. The method of claim 10, wherein said step of correcting said ocular chromatic aberration further comprises providing a bandpass filter for correcting said ocular chromatic aberration.

12. The method of claim 10, wherein said step of correcting said ocular chromatic aberration further comprises providing a long-pass filter for correcting said ocular chromatic aberration.

13. The method of claim 10, further comprising providing an apodization filter for correcting said aberration.

14. The method of claim 13, wherein said apodization filter provides a non uniform amplitude transmission across the eye's pupil.

15. The method of claim 14, wherein the amplitude transmission increases from the edge to the center of the pupil.

16. The method of claim 1, wherein correcting ocular chromatic aberration comprises apodizing a person's pupil.

17. The method of claim 16, wherein said apodization provides a non uniform light amplitude transmission between an edge portion and the center of the pupil.

18. The method of claim 17, wherein the light transmission increases from the edge to the center of the pupil.

19. The method of claim 17, wherein said apodization is a function of wavelength.

20. The method of claim 1, wherein the correction of the ocular chromatic aberration is provided integrally with the correction of the higher-order monochromatic aberration.

21. The method of claim 1 wherein the correction of the ocular chromatic aberration is provided externally to the correction of the higher-order monochromatic aberration.

22. The method of claim 1, further comprising measuring at least one of the ocular higher-order monochromatic aberrations and the ocular chromatic aberration.

23. An ocular device for improving a person's vision, comprising:
an optical component selected from at least one of a contact lens, an IOL, an inlay and an onlay, wherein said component has a surface shape adapted to correct a higher-order monochromatic ocular wave aberration of the person's eye and further wherein said component is adapted to correct an ocular chromatic aberration.

24. The ocular device of claim 23, wherein said higher-order monochromatic ocular wave aberration comprises third and higher-order radial Zernicke modes.

25. The ocular device of claim 24, wherein said higher-order monochromatic ocular wave aberration comprises fifth to tenth-order radial Zernicke modes.

26. The ocular device of claim 25, wherein said component adapted to correct chromatic aberration is a light filter.

27. The ocular device of claim 26, wherein said light filter is a neutral density filter.

28. The ocular device of claim 26, wherein said light filter is a bandpass filter.

29. The ocular device of claim 26, wherein said light filter is a long-pass filter.

30. The ocular device of claim 26, wherein said light filter is an apodization filter.

31. The ocular device of claim 30, wherein said apodization filter has a non uniform amplitude transmission between a center and an edge of the pupil.

32. The ocular device of claim 31, wherein the amplitude transmission decreases from the center to the edge of the pupil.

33. The ocular device of claim 31, wherein the apodization filter has a spectrally dependent, non uniform amplitude transmission between a center and an edge of the pupil.

34. The ocular device of claim 33, wherein the attenuation of the light from the center to the edge of the pupil increases for wavelengths as said wavelengths move away from a reference wavelength.

35. The ocular device of claim 30, wherein said apodization filter is represented by a super-Gaussian function of the form $A(r)=\exp(-r^4/2\sigma^2)$.

36. The ocular device of claim 30, wherein said apodization filter comprises an annulus of color absorbing material having an increasing density from the center to the edge of the pupil.

37. The ocular device of claim 36, wherein said apodization filter has a total band pass from about 500 nm to about 650 nm.

38. The ocular device of claim 30, wherein said apodization filter comprises a plurality of adjacent annular shaped filters wherein each annular filter has a defined bandpass with a bandwidth that is narrower than an adjacent smaller annulus.

39. The ocular device of claim 30, wherein said apodization filter comprises annulus having an inner diameter across which there is no light filtering and a portion between the inner diameter and an outer diameter having a passband with a bandwidth from about 550 nm to 610 nm.

40. The ocular device of claim 39, wherein said inner radius is equal to or less than 2 mm.

41. The ocular device of claim 30, wherein said apodization filter comprises a plurality of ad accent annular shaped filters wherein a central radial portion of the component provides no filtering, a first annular ring provides a long pass filter, and a second annular ring adjacent to and larger than the first annular ring provides a bandpass filter.

42. The ocular device of claim 41, wherein the long pass filter provides transmission for wavelengths greater than about 510 nm, and the bandpass filter provides transmission between about 550 nm to 610 nm.

43. The ocular device of claim 30, wherein said apodization filter comprises a long-pass filter.

44. The ocular device of claim 43, wherein said long-pass filter substantially transmits wavelengths above a reference wavelength of about 555 nm.

45. An optical system for improving a person's vision, comprising:
a higher-order phase compensation element; and
a light amplitude modifying element.

46. The optical system of claim 45, wherein the higher-order phase compensation element and the light amplitude modifying element are resident in a common optical component.

47. The optical system of claim 46, wherein the common optical component comprises at least one of a contact lens, an IOL, an inlay and an onlay.

48. The optical system of claim 45, wherein the higher-order phase compensation element and the light amplitude modifying element are each resident in a separate optical component.

49. The optical system of claim 48, wherein the phase compensation element is resident in at least one of a contact lens, an IOL, an inlay, an onlay and a reshaped cornea, and the light amplitude modifying element is resident in at least one of a contact lens, an IOL, an inlay, an onlay and an external optical component used in conjunction with the phase compensation element.

50. The optical system of claim 45, wherein the higher-order phase compensation element is a deformable mirror.

51. The optical system of claim 45, wherein the higher-order phase compensation element is a liquid crystal device.

52. The optical system of claim 45, wherein the higher-order phase compensation element is a contact lens.

53. The optical system of claim 45, wherein the higher-order phase compensation element is an IOL.

54. The optical system of claim 45, wherein the higher-order phase compensation element is a reshaped cornea.

55. The optical system of claim 45, wherein the higher-order phase compensation element is an ocular inlay.

56. The optical system of claim 45, wherein the higher-order phase compensation element is an ocular onlay.

57. The optical system of claim 45, wherein the light amplitude modifying element is a filter.

58. The optical system of claim 57, wherein the filter is at least one of a passband filter and a long-pass filter.

59. The optical system of claim 45, wherein the light amplitude modifying element is an apodized pupil of the person.

60. The optical system of claim 59, wherein the apodized pupil comprises a non uniform amplitude transmission of light between a center and an edge of the pupil.

61. The optical system of claim 59, wherein the apodized pupil comprises a spectrally dependent, non uniform amplitude transmission of light between a center and an edge of the pupil.

62. The optical system of claim 45, wherein the phase compensation element and the light amplitude modifying element are disposed on an optical axis of the optical system.

63. An optical system for generating high resolution images of the retina of the living eye, comprising:

means for generating a reflected point source image of the retina of said living eye;

means for receiving said reflected point source image and for converting said point source image to corresponding digital signals;

computer means for calculating a higher order monochromatic aberration using, said digital signals;

means for illuminating a retinal disk on said living eye for producing a retinal disk image;

a higher-order phase compensating optical element in an optical path of the system, said compensating optical element being adjusted to correct said higher-order monochromatic aberrations;

a light amplitude modifying element for correcting chromatic aberration disposed in the optical path of the system; and means for providing an image of said reflected retinal disk image after correction of the higher order monochromatic aberration and the chromatic aberration.

64. The system of claim 63, wherein said higher-order phase compensating optical element is one of a deformable mirror, a liquid crystal device, and a MEMS device.

65. The system of claim 63, wherein said light amplitude modifying element is one of an artificial apodization element and an optical filter.

66. A method for generating high resolution images of the retina of the living eye, comprising the steps of:

generating a reflected point source image of the retina of said living eye;

converting said point source image to corresponding digital signals;

calculating a higher-order monochromatic wavefront aberration using said digital signals;

illuminating a retinal disk on said living eye for producing a retinal disk image;

intercepting said retinal disk image with a higher-order phase compensating optical element, said compensating optical element being adjusted such that wavefront compensation for said wave aberrations is provided for said living eye; and providing a light amplitude modifying element for correcting chromatic aberration.

67. The method of claim 66, wherein illuminating the retinal disk comprises using a broadband light source.

68. The method of claim 66, wherein the step of correcting the chromatic aberration comprises artificially apodizing a pupil of the optical system.

* * * * *